(12) United States Patent
Inoue

(10) Patent No.: US 11,911,146 B2
(45) Date of Patent: Feb. 27, 2024

(54) LIVING BODY DETECTION DEVICE USING NON-CONTACT SENSOR, LIVING BODY DETECTION METHOD, AND RECORDING MEDIUM

(71) Applicant: Panasonic Intellectual Property Management Co., Ltd., Osaka (JP)

(72) Inventor: Kenichi Inoue, Osaka (JP)

(73) Assignee: PANASONIC INTELLECTUAL PROPERTY MANAGEMENT CO., LTD., Osaka (JP)

(*) Notice: Subject to any disclaimer, the term of this patent is extended or adjusted under 35 U.S.C. 154(b) by 715 days.

(21) Appl. No.: 17/089,833

(22) Filed: Nov. 5, 2020

(65) Prior Publication Data
US 2021/0052194 A1 Feb. 25, 2021

Related U.S. Application Data

(63) Continuation of application No. PCT/JP2019/018316, filed on May 8, 2019.

(30) Foreign Application Priority Data

May 28, 2018 (JP) ................................. 2018-101698
Mar. 25, 2019 (JP) ................................. 2019-056121

(51) Int. Cl.
*A61B 5/11* (2006.01)
*A61B 5/00* (2006.01)
(Continued)

(52) U.S. Cl.
CPC ................ *A61B 5/11* (2013.01); *A61B 5/746* (2013.01); *G01S 13/56* (2013.01); *G01S 13/581* (2013.01); *G01S 13/88* (2013.01); *G06M 11/00* (2013.01)

(58) Field of Classification Search
CPC .......... A61B 5/11; A61B 5/746; A61B 5/024; A61B 5/0507; A61B 5/1135;
(Continued)

(56) References Cited

U.S. PATENT DOCUMENTS 5,047,750 A * 9/1991 Hector ............... G08B 21/0227
340/573.4
5,218,344 A * 6/1993 Ricketts ............... G08B 25/016
379/38
(Continued)

FOREIGN PATENT DOCUMENTS

JP 51-139369 A 12/1976
JP 7-237837 A 9/1995
(Continued)

OTHER PUBLICATIONS

International Search Report of PCT application No. PCT/JP2019/018316 dated Jun. 4, 2019.

*Primary Examiner* — Curtis J King
(74) *Attorney, Agent, or Firm* — GREENBLUM & BERNSTEIN, P.L.C.

(57) ABSTRACT

A living body detection device includes a receiver that receives, from at least one non-contact sensor, a measurement result obtained by measuring a detection area with the at least one non-contact sensor, an extraction circuit that extracts a biological signal from the measurement result, a counting circuit that counts the number of living bodies present in the detection area from the biological signal, and an acquisition circuit that acquires a prescribed number of living bodies to be present in the detection area, and a verification circuit that verifies whether the number of living bodies counted by the counting circuit is equal to the prescribed number and outputs a result of verification.

14 Claims, 18 Drawing Sheets

(51) Int. Cl.
  *G01S 13/56* (2006.01)
  *G01S 13/58* (2006.01)
  *G01S 13/88* (2006.01)
  *G06M 11/00* (2006.01)

(58) Field of Classification Search
  CPC ..... A61B 5/6889; G01S 13/56; G01S 13/581; G01S 13/88; G01S 7/539; G01S 13/584; G01S 15/523; G01S 7/415; G06M 11/00
  See application file for complete search history.

(56) References Cited

U.S. PATENT DOCUMENTS

| | | | | |
|---|---|---|---|---|
| 5,465,115 | A * | 11/1995 | Conrad | H04N 7/18 348/170 |
| 6,307,475 | B1 * | 10/2001 | Kelley | G01S 13/56 340/567 |
| 7,019,644 | B2 * | 3/2006 | Barrie | G07C 9/27 340/8.1 |
| 9,858,632 | B1 * | 1/2018 | Shipman, Jr. | G06Q 50/26 |
| 10,366,599 | B1 * | 7/2019 | Hodge | G08B 21/0269 |
| 11,538,125 | B1 * | 12/2022 | Shipman, Jr. | G07C 9/37 |
| 11,669,981 | B2 * | 6/2023 | Steiner | G06T 7/136 382/103 |
| 2002/0063627 | A1 * | 5/2002 | Makiyama | G07C 9/28 340/568.1 |
| 2002/0084903 | A1 * | 7/2002 | Chaco | G08B 21/0208 340/573.4 |
| 2002/0101353 | A1 * | 8/2002 | Radomsky | G08B 21/0227 340/573.4 |
| 2002/0167408 | A1 * | 11/2002 | Trajkovic | G06Q 30/06 340/995.22 |
| 2003/0058111 | A1 * | 3/2003 | Lee | G08B 13/19641 348/E7.086 |
| 2003/0208692 | A9 * | 11/2003 | Kimmel | G08B 13/19684 340/511 |
| 2004/0080419 | A1 * | 4/2004 | Martin | G08B 21/0286 340/568.1 |
| 2004/0150520 | A1 * | 8/2004 | Barrie | G07C 9/27 340/8.1 |
| 2005/0035862 | A1 * | 2/2005 | Wildman | G08B 13/2462 340/572.1 |
| 2005/0156759 | A1 * | 7/2005 | Aota | G08G 1/127 235/376 |
| 2006/0017564 | A1 * | 1/2006 | Phillips | G06K 17/00 340/539.13 |
| 2008/0297341 | A1 * | 12/2008 | McClanahan | G07C 9/28 340/573.6 |
| 2009/0027211 | A1 * | 1/2009 | Cutler | E04H 4/06 340/573.6 |
| 2010/0162285 | A1 * | 6/2010 | Cohen | H04N 21/262 725/12 |
| 2010/0246970 | A1 * | 9/2010 | Springer | A01K 11/006 340/572.1 |
| 2011/0291832 | A1 * | 12/2011 | Al-Kadi | H05B 47/115 340/541 |
| 2013/0324166 | A1 * | 12/2013 | Mian | H04W 4/029 455/457 |
| 2014/0139633 | A1 * | 5/2014 | Wang | H04N 7/18 348/46 |
| 2014/0266703 | A1 * | 9/2014 | Dalley, Jr. | G08B 25/00 340/10.51 |
| 2014/0266704 | A1 * | 9/2014 | Dalley, Jr. | G08B 21/18 340/539.13 |
| 2014/0266726 | A1 * | 9/2014 | Dalley, Jr. | G08B 13/2451 340/572.1 |
| 2014/0355829 | A1 * | 12/2014 | Heu | G06T 7/20 382/103 |
| 2016/0035205 | A1 * | 2/2016 | Messenger | G16H 40/67 340/539.15 |
| 2016/0139576 | A1 * | 5/2016 | Aiken | F24F 11/30 315/297 |
| 2016/0150362 | A1 * | 5/2016 | Shaprio | H05K 5/0086 340/539.13 |
| 2016/0274663 | A1 * | 9/2016 | Aoyama | G09B 5/02 |
| 2017/0112434 | A1 * | 4/2017 | Lane | A61B 5/6814 |
| 2017/0220829 | A1 * | 8/2017 | Argentieri | G06Q 10/06 |
| 2017/0357856 | A1 * | 12/2017 | Hu | G01J 5/0025 |
| 2017/0364817 | A1 * | 12/2017 | Raykov | G06N 20/10 |
| 2018/0150738 | A1 * | 5/2018 | Harvey | G06K 7/10297 |
| 2018/0192919 | A1 * | 7/2018 | Nakayama | A61B 5/1116 |
| 2018/0199836 | A1 * | 7/2018 | Hamada | A61B 5/02416 |
| 2019/0294949 | A1 * | 9/2019 | Harvey | G06K 19/0711 |
| 2019/0333233 | A1 * | 10/2019 | Hu | G01S 13/04 |
| 2019/0383921 | A1 * | 12/2019 | Argentieri | G08B 21/22 |
| 2020/0064784 | A1 * | 2/2020 | Steiner | G01S 13/34 |
| 2020/0125838 | A1 * | 4/2020 | Dalley, Jr. | H04N 23/617 |
| 2020/0202474 | A1 * | 6/2020 | Asukai | G06Q 10/06315 |
| 2020/0219623 | A1 * | 7/2020 | Kushida | G16H 50/80 |
| 2020/0221977 | A1 * | 7/2020 | Tanaka | G08B 21/0415 |
| 2020/0244380 | A1 * | 7/2020 | Agrawal | G06F 3/0482 |
| 2021/0204522 | A1 * | 7/2021 | Kameyama | H04N 7/18 |
| 2021/0396861 | A1 * | 12/2021 | Wellig | G01S 13/04 |
| 2022/0044064 | A1 * | 2/2022 | Zhang | G06V 20/44 |
| 2023/0126895 | A1 * | 4/2023 | Baker | G01S 13/584 342/146 |

FOREIGN PATENT DOCUMENTS

| | | |
|---|---|---|
| JP | 2009-245213 | 10/2009 |
| JP | 2015-011597 A | 1/2015 |

* cited by examiner

| DIRECTIVITY | RANGE BIN | REFLECTION INTENSITY | PHASE ROTATION AMOUNT |
|---|---|---|---|
| 1 | 1 | $i_{11}$ | $r_{11}$ |
|  | ⋮ | ⋮ | ⋮ |
|  | n | $i_{1n}$ | $r_{1n}$ |
| ⋮ | ⋮ | ⋮ | ⋮ |
| m | 1 | $i_{m1}$ | $r_{m1}$ |
|  | ⋮ | ⋮ | ⋮ |
|  | n | $i_{mn}$ | $r_{mn}$ |

LIVING BODY DETECTION DEVICE USING NON-CONTACT SENSOR, LIVING BODY DETECTION METHOD, AND RECORDING MEDIUM

BACKGROUND

1. Technical Field

The present disclosure relates to a living body detection device that uses a non-contact sensor, a living body detection method, and a recording medium that stores a program for detecting a living body.

2. Description of the Related Art

In recent years, a variety of systems that use a biometric detection technology have been put to practical use. For example, monitoring systems for, for example, children in childcare centers, residents in care facilities, and patients in hospitals are application examples of a living body detection technology. In monitoring the activities of these people, the effect of interference between people and the effect of dead spots need to be minimized to ensure that a target person in a detection area is properly detected.

The situation where it is important to properly detect a target person is not limited to a scene of monitoring. For example, according to the customer attraction information providing system described in Japanese Unexamined Patent Application Publication No. 2009-245213, at, for example, an exhibition, the system properly detects a visitor in each of booths by identifying the location of a mobile station carried by an individual visitor and provides congestion information to visitors.

SUMMARY

In one general aspect, the techniques disclosed here feature a living body detection device including a receiver that receives, from at least one non-contact sensor, a measurement result obtained by measuring a detection area with the at least one non-contact sensor, an extraction circuit that extracts a biological signal from the measurement result, a counting circuit that counts the number of living bodies present in the detection area based on the biological signal, an acquisition circuit that acquires a prescribed number of living bodies to be present in the detection area, and a verification circuit that verifies whether the number of living bodies counted by the counting circuit is equal to the prescribed number and outputs a result of verification.

It should be noted that general or specific embodiments may be implemented as a system, a method, an integrated circuit, a computer program, a computer-readable recording medium, such as a compact disc read only memory (CD-ROM), or any selective combination thereof.

Additional benefits and advantages of the disclosed embodiments will become apparent from the specification and drawings. The benefits and/or advantages may be individually obtained by the various embodiments and features of the specification and drawings, which need not all be provided in order to obtain one or more of such benefits and/or advantages.

DETAILED DESCRIPTION

Figure 1:
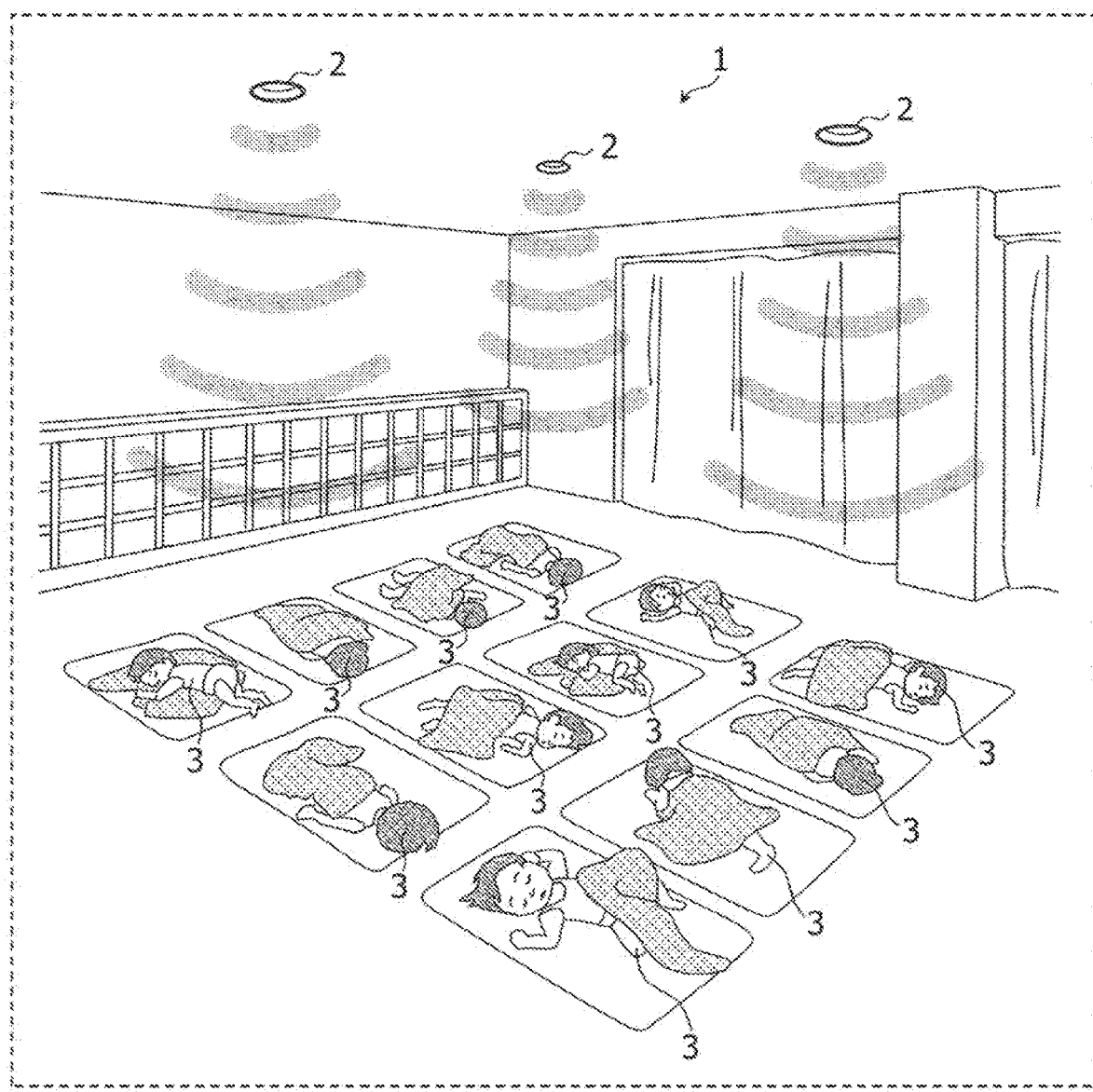
FIG. 1 is a schematic illustration of an application example of a living body detection device according to a first embodiment.

Underlying Knowledge Forming Basis of the Present Disclosure

According to the customer attraction information providing system described in Japanese Unexamined Patent Application Publication No. 2009-245213, it is assumed that a visitor is carrying a mobile station. Accordingly, the system identifies the location of the mobile station and, thus, properly detects a visitor at each booth.

However, it is difficult for a target person to carry a mobile station at all times when being monitored in, for example, a childcare center or a care facility. This is because the target person often forgets, loses, or intentionally removes the mobile station therefrom, for example. The mobile station may be embedded in the clothing of the target person or be attached directly to the body of the target person to force the target person to carry the mobile station, but the workload imposed on the childcare worker or caregiver may increase. In addition, the target person's comfort may be compromised.

The present inventor has studied this problem and has conceived the idea of a living body detection device, a living body detection method, a recording medium, and a program capable of reducing the risk of a false negative in the target person detection.

According to an aspect of the present disclosure, a living body detection device includes a receiver that receives, from at least one non-contact sensor, a measurement result obtained by measuring a detection area with the at least one non-contact sensor, an extraction circuit that extracts a biological signal from the measurement result, a counting circuit that counts the number of living bodies present in the detection area based on the biological signal, and an acquisition circuit that acquires a prescribed number of living bodies to be present in the detection area, and a verification circuit that verifies whether the number of living bodies counted by the counting circuit is equal to the prescribed number and outputs the result of verification.

According to such a configuration, since the measurement result obtained by measuring the target person with the non-contact sensor is used, the target person need not carry any equipment. In addition, it is verified whether the number of living bodies counted on the basis of the measurement result output from the non-contact sensor is equal to the prescribed number. Accordingly, if the number of living bodies counted is not equal to the prescribed number, a false negative in the target person detection can be found and, thus, the processing for coping with a false negative can be performed. As a result, a living body detection device capable of reducing the risk of a false negative in the target person detection is achieved.

The living body detection device may further include a notified that provides notification of a false negative when the number of living bodies counted by the counting circuit is not equal to the prescribed number.

According to such a configuration, as a process for coping with a false negative, a process of notifying a user of a false negative can be performed to prompt the user to take an appropriate action.

The living body detection device may further include a mover that moves the at least one non-contact sensor when the number of living bodies counted by the counting circuit is not equal to the prescribed number.

According to such a configuration, by moving the non-contact sensor if a false negative occurs, the false negative can be eliminated without user intervention.

The at least one non-contact sensor may be capable of switching between a directional mode in which the at least one non-contact sensor has directivity and an omnidirectional mode in which the at least one non-contact sensor does not have directivity. The living body detection device may further include a controller that instructs the at least one non-contact sensor to operate in the directional mode when the number of living bodies counted by the counting circuit is not equal to the prescribed number.

According to such a configuration, if a false negative occurs, the non-contact sensor is operated in the directional mode to detect the target persons individually by directivity. As a result, a false negative can be eliminated without user intervention.

When the at least one non-contact sensor is in the directional mode, the at least one non-contact sensor may measure the detection area in a first state having a first directivity and in a second state having a second directivity that is different from the first directivity. The receiver may receive, from the at least one non-contact sensor, a first measurement result that is obtained in the first state and a second measurement result that is obtained in the second state. The extraction circuit may extract a first biological signal from the first measurement result and extract a second biological signal from the second measurement result. The counting circuit may count the first number of living bodies based on the first biological signal and counts the second number of living bodies based on the second biological signal, and the verification circuit may verify whether the sum of the first number of living bodies and the second number of living bodies is equal to the prescribed number.

According to such a configuration, the target persons at different azimuths are distinguishably counted on the basis of different directivities. As a result, a false negative in the target person detection can be found more accurately.

The at least one non-contact sensor may include a plurality of non-contact sensors, and the receiver may receive the measurement result from each of the plurality of non-contact sensors. The extraction circuit may extract the biological signal from the measurement result output from each of the plurality of non-contact sensors. The counting circuit may count the number of living bodies on a basis of the biological signal for each of the plurality of non-contact sensors. The verification circuit may further verify whether at least one of the plurality of non-contact sensors detects the number of living bodies that is equal in number to the prescribed number.

According to such a configuration, since the measurement result obtained by measuring the target person with the plurality of non-contact sensors is used, a false negative in the target person detection is less likely to occur. In addition, it is verified whether at least one non-contact sensor senses a number of living bodies that is equal in number to the prescribed number. Accordingly, if the count result is not equal to the prescribed number for all the non-contact sensors, a false negative in the target person detection can be found. As a result, a living body detection device can be achieved that is capable of reducing the risk of a false negative in the target person detection while reducing excessive notification of a false negative.

Each of the plurality of non-contact sensors may be capable of switching between an operation mode in which the living body detection device is capable of measuring the detection area and an idle mode in which the living body detection device does not measure the detection area and is ready for measuring the detection area. The living body detection device may further include a controller that instructs, among the plurality of non-contact sensors, a non-contact sensor that has detected the number of living bodies that is not equal to the prescribed number to enter the idle mode.

According to such a configuration, by causing the non-contact sensor that has not sensed a number of target persons that is not equal in number to the prescribed number to enter the idle mode, the power consumption can be reduced, and the amount of electromagnetic radiation absorbed by the target person can be reduced.

In addition, the controller may periodically instruct, among the plurality of non-contact sensors, the non-contact sensor in the idle mode to enter the operation mode.

According to such a configuration, the non-contact sensor that can detect all the target persons again due to, for example, the movement of the target person can be operated again. As a result, the target persons can be continuously and properly detected.

The at least one non-contact sensor may be a Doppler radar.

According to such a configuration, by using a Doppler radar, the distance to the target object and the movement of the target object can be stably measured. Thus, a living body detection device having an excellent t living body detection performance can be achieved.

According to an aspect of the present disclosure, a living body detection method includes receiving, from at least one non-contact sensor, a measurement result obtained by measuring a detection area with the at least one non-contact sensor, extracting a biological signal from the measurement result, counting the number of living bodies present in the detection area on a basis of the biological signal, and verifying whether the number of living bodies counted in the counting is equal to a prescribed number of living bodies and outputting a result of verification.

Since the method uses the measurement result obtained by measuring a target person with a non-contact sensor, the target person need not carry any equipment. In addition, since it is verified whether the counted number of living bodies in the measurement result output from the non-contact sensor is equal to the prescribed number, a false negative in the target person detection is found by inequality between the counted number of living bodies and the prescribed number. As a result, a living body detection method that reduces the risk of a false negative in the target person detection can be provided.

According to an aspect of the present disclosure, a computer-readable recording medium is a computer-readable recording medium that stores a program for detecting a living body. When the program is executed by a computer, the following processes are performed: receiving, from at least one non-contact sensor, a measurement result obtained by measuring a detection area with the at least one non-contact sensor, extracting a biological signal from the measurement result, counting the number of living bodies present in the detection area on a basis of the biological signal, and verifying whether the number of living bodies counted in the counting is equal to a prescribed number of living bodies and outputting a result of verification.

According to an aspect of the present disclosure, a program is a computer-executable program for detecting a living body. The program causes a computer to perform the following processes: receiving, from at least one non-contact sensor, a measurement result obtained by measuring a detection area with the non-contact sensor, extracting a biological signal from the measurement result, counting the number of living bodies present in the detection area on a basis of the biological signal, and verifying whether the number of living bodies counted in the counting is equal to the prescribed number of living bodies and outputting a result of verification.

Such a configuration can cause a computer to execute a living body detection method having the same effect as described above.

In the present disclosure, all or a part of any of circuit, unit, device, part or portion, or any of functional blocks in the block diagrams may be implemented as one or more of electronic circuits including, but not limited to, a semiconductor device, a semiconductor integrated circuit (IC) or an LSI. The LSI or IC can be integrated into one chip, or also can be a combination of plural chips. For example, functional blocks other than a memory may be integrated into one chip. The name used here is LSI or IC, but it may also be called system LSI, VLSI (very large scale integration), or ULSI (ultra large scale integration) depending on the degree of integration. A Field Programmable Gate Array (FPGA) that can be programmed after manufacturing an LSI or a reconfigurable logic device that allows reconfiguration of the connection or setup of circuit cells inside the LSI can be used for the same purpose.

Further, it is also possible that all or a part of the functions or operations of the circuit, unit, device, part or portion are implemented by executing software. In such a case, the software is recorded on one or more non-transitory recording media such as a ROM, an optical disk or a hard disk drive, and when the software is executed by a processor, the software causes the processor together with peripheral devices to execute the functions specified in the software. A system or apparatus may include such one or more non-transitory recording media on which the software is recorded and a processor together with necessary hardware devices, such as an interface.

A living body detection device according to an aspect of the present disclosure is described in detail below with reference to the accompanying drawings.

It should be noted that each of the embodiments described below is a particular example of the present disclosure. A numerical value, a shape, a material, a constituent element, the positions and the connection form of the constituent elements, steps, and the sequence of steps described in the embodiments are only examples and shall not be construed as limiting the scope of the present disclosure. In addition, among the constituent elements in the embodiments described below, the constituent element that does not appear in an independent claim, which has the broadest scope, is described as an optional constituent element.

First Embodiment

FIG. 1 is a schematic illustration of an application example of a living body detection device according to the first embodiment, in which a monitoring system for detecting an infant in a childcare center is illustrated as an example. The living body detection device in a monitoring system 1 uses one or more (three in FIG. 1) non-contact sensors 2 to detect one or more (12 in FIG. 1) infants 3 who are the target persons.

In the monitoring system 1, for example, by detecting the breathing or the heartbeat of each of the infants 3, it is confirmed that all the infants 3 are healthy. Therefore, in the monitoring system 1, it is important that all the infants 3 be individually detected.

The living body detection device in the monitoring system 1 counts the number of infants 3 in a detection area from the measurement result output from the non-contact sensor 2. If the counted number of infants 3 is not equal to the prescribed number, the living body detection device performs a process for coping with a false negative. For example, the process for coping with a false negative may be a process for notifying a user of the living body detection device of a false negative and prompting the user to take an appropriate action. For example, in the case of a nursery school, a nursery teacher may be notified of a false negative detection. Accordingly, the nursery teacher visually counts the number of infants 3.

Figure 2:
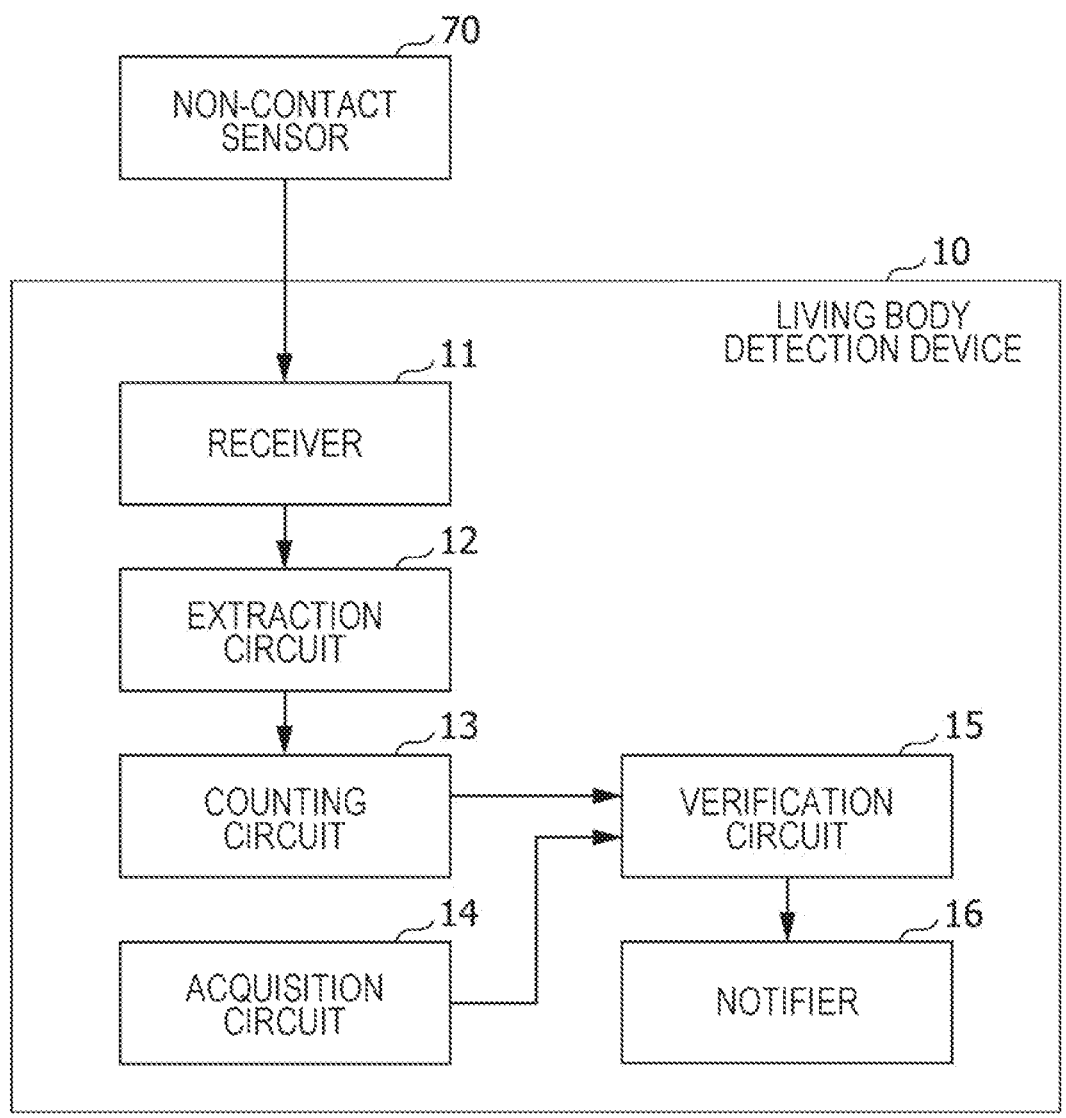
FIG. 2 is a block diagram illustrating an example of the functional configuration of the living body detection device according to the first embodiment.

FIG. 2 is a block diagram of an example of the functional configuration of a living body detection device 10. In FIG. 2, a non-contact sensor 70 is illustrated together with the living body detection device 10. The non-contact sensor 70 may be included in the living body detection device 10. The non-contact sensor 70 corresponds to the non-contact sensor 2 in FIG. 1.

The non-contact sensor 70 is described first. The non-contact sensor 70 measures the distance to a target object in a detection area and the movement of the target object in a non-contact manner. The non-contact sensor 70 includes, for example, a Doppler radar. The Doppler radar emits ultrasonic waves or electromagnetic waves serving as detection waves toward the detection area and receives reflected waves from the target object. Thus, the Doppler radar measures the distance to the target object and the movement of the target object in a non-contact manner. For simplicity, the non-contact sensor 70 measures a target object in an omnidirectional mode in which neither the directivity of the detection waves nor the directivity of the reflected waves is controlled.

Figure 3:
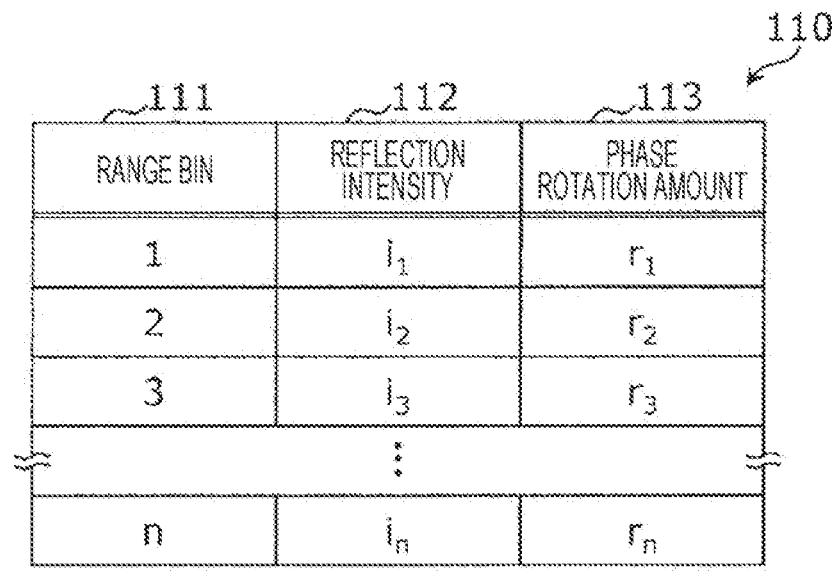
FIG. 3 illustrates an example of measurement results of a non-contact sensor according to the first embodiment.

FIG. 3 is a diagram illustrating an example of the measurement result output from the non-contact sensor 70. As illustrated in FIG. 3, a measurement result 110 output from the non-contact sensor 70 includes a reflection intensity 112 and a phase rotation amount 113 for each of range bins 111.

The range bin 111 represents an index of the discrete measurement result of the distance from the non-contact sensor 70 to a target object. The distance of the range bin 111 corresponds to the one-way travel time from the time of emission of the detection wave to the time of reception of the reflected wave. The width of the range bin 111, that is, the resolution of distance is, for example, 7.5 cm when the detection wave is a radio wave in the millimeter wave band with a pulse width of 0.5 nanoseconds. The reflection intensity 112 is the intensity of the reflected wave and represents the degree of certainty of a target object being in the corresponding range bin. The phase rotation amount 113 is the amount of change in phase between the detection wave and the reflected wave, and its time change corresponds to the relative speed of the target object. Note that the relative speed of the target object means a velocity component in the line-of-sight direction when the target object is viewed from the non-contact sensor 70.

The description of the living body detection device 10 is continued. Referring back to FIG. 2, the living body detection device 10 includes a receiver 11, an extraction circuit 12, a counting circuit 13, an acquisition circuit 14, a verification circuit 15, and a notifier 16.

The receiver 11 receives the measurement result obtained by measuring the target object in the detection area by the non-contact sensor 70. The measurement result may represent the distance to the target object and the movement of the target object. The extraction circuit 12 extracts a biological signal from the measurement result. The counting circuit 13 counts the number of living bodies in the detection area from the extracted biological signal.

The acquisition circuit 14 acquires the prescribed number of living bodies to be present in the detection area. The verification circuit 15 verifies whether the counted number of living bodies is equal to the prescribed number and outputs the verification result. The notifier 16 provides notification of a false negative result if the counted number of living bodies is not equal to the prescribed number.

The living body detection device 10 is configured as, for example, a computer system including, for example, a processor, a memory, and a communication circuit. Each of the constituent element of the living body detection device 10 illustrated in FIG. 2 may be, for example, a software function performed by the processor executing a program recorded in a memory.

The operation performed by the living body detection device 10 configured as described above is described below with reference to a specific example of a measurement situation.

Figure 4:
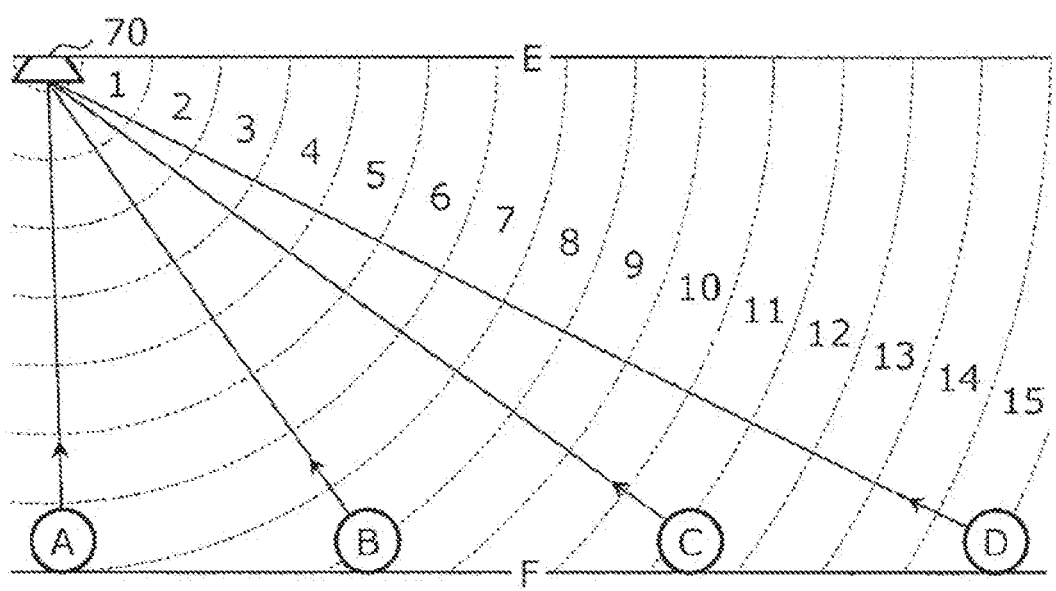
FIG. 4 is a schematic illustration of an example of a measurement situation according to the first embodiment.

FIG. 4 is a schematic illustration of an example of a measurement situation. In FIG. 4, the non-contact sensor 70 is disposed on a ceiling E, and four target persons A, B, C, and D are located on a floor F. In addition, in FIG. 4, an area between neighboring concentric circles represents a range bin, and the numbers arranged in the radial direction of the concentric circles represent the range bin numbers. In a 3D view, the range bin is a concentric spherical shell region that spreads in all directions (in three dimensions).

Figure 5:
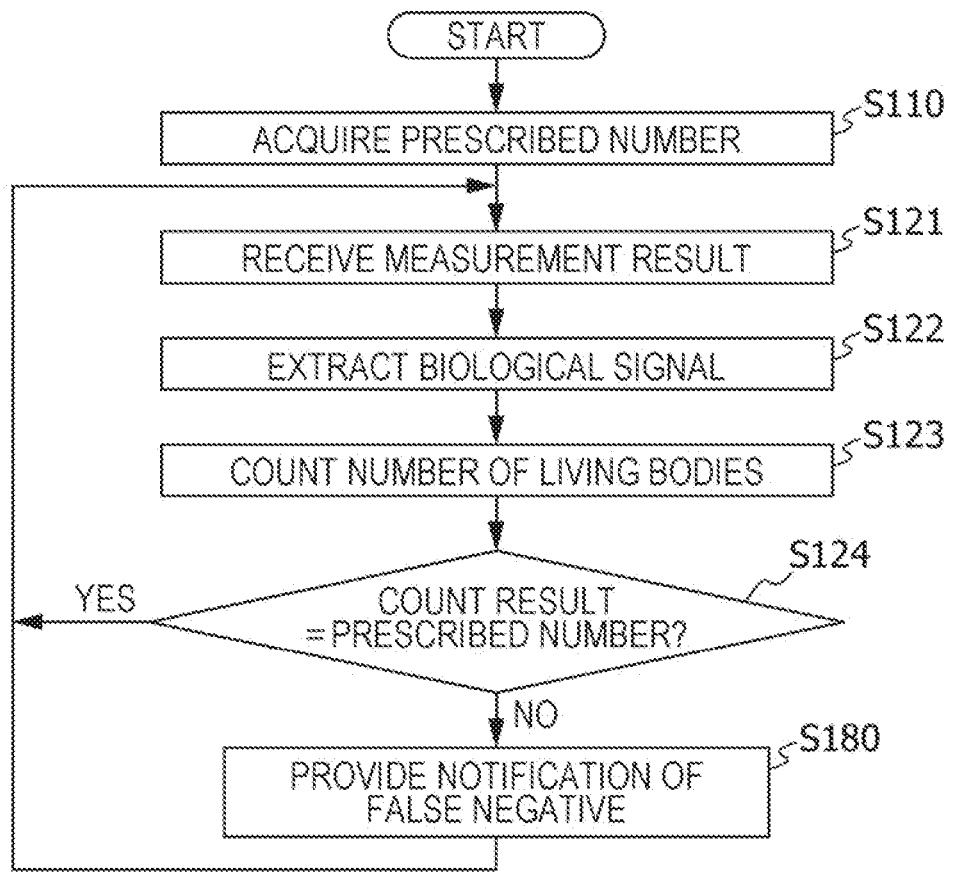
FIG. 5 is a flowchart illustrating an example of the operation performed by the living body detection device according to the first embodiment.

FIG. 5 is a flowchart illustrating an example of the operation performed by the living body detection device 10.

The living body detection device 10 operates in a manner described below in accordance with a flowchart illustrated in FIG. 5 in the measurement situation illustrated in FIG. 4.

The acquisition circuit 14 acquires the prescribed number (S110). The prescribed number is the number of living bodies scheduled to be present in the detection area. That is, the prescribed number indicates the number of target persons to be detected by the living body detection device 10. For example, in the case of a nursery school, the acquisition circuit 14 may acquire the number of infants in the nursery school from an attendance register system or may acquire the numerical value input by a nursery teacher using a terminal device. In the example illustrated in FIG. 4, the acquired prescribed number is four.

The receiver 11 receives the measurement result from the non-contact sensor 70 (S121), and the extraction circuit 12 extracts a biological signal from the measurement result (S122).

Figure 6:
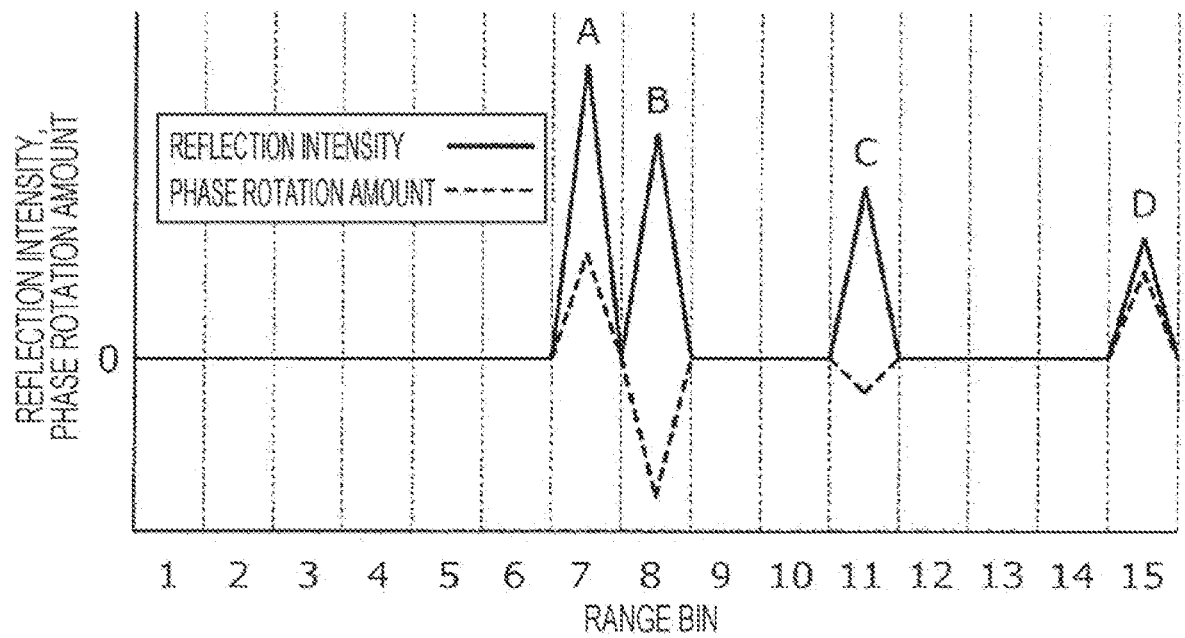
FIG. 6 is a graph illustrating an example of the measurement results according to the first embodiment.

FIG. 6 is a graph illustrating an example of the measurement result corresponding to the measurement situation illustrated in FIG. 4. In the example illustrated in FIG. 6, the reflection intensities of the reflected waves and the phase rotation amount due to the body movement, such as the breathing and the heartbeat, are detected from the target persons A, B, C, and D present in the seventh, eighth, eleventh, and fifteenth range bins, respectively.

Figure 7:
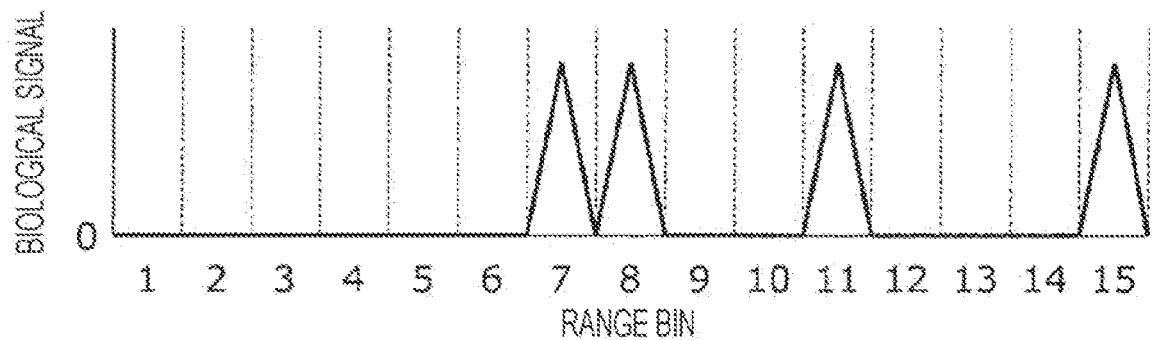
FIG. 7 is a graph illustrating an example of a biological signal according to the first embodiment.

FIG. 7 is a graph illustrating an example of a biological signal extracted from the time series measurement result illustrated in FIG. 6. The biological signal is, for example, a score based on the reflection intensity and the magnitude of a specific frequency component included in the time series of phase rotation amount. The score represents the degree of certainty of a living body being in each of the range bin. The above-mentioned reflection intensity represents the degree of certainty of the presence of a target object, and the target object may be a non-living body. In addition, the magnitude of the specific frequency component mentioned above represents the degree of certainty of the target object being a living body. The specific frequency component is a frequency component of several Hz or less, which corresponds to a body movement due to the breathing or heartbeat. For example, the specific frequency component is acquired from the time series of phase rotation amount by using a lowpass filter or a trend removal filter.

In the example illustrated in FIG. 7, a biological signal is extracted in each of the seventh, eighth, eleventh, and fifteenth range bins. The biological signal may be simply a binary signal indicating whether a living body is present or not.

Note that if the distance resolution of the non-contact sensor 70 is sufficiently high, the displacement of the body surface of a target person can be detected from a change in the range bin having the peak of the reflection intensity. In this case, the biological signal may be obtained on the basis of the time series of displacement of the body surface of the target person, that is, the frequency component due to the breathing or heartbeat included in the change in the range bin having the peak of the reflection intensity.

Referring back to FIG. 5, the counting circuit 13 counts the number of living bodies in the detection area from the extracted biological signals (S123). The number of living bodies may be counted, for example, by the number of range bins from which a biological signal larger than a threshold value is extracted or by the number of peaks appearing in the graph of the biological signal. In the example illustrated in FIG. 7, the number of living bodies is counted as four.

The verification circuit 15 verifies whether the counted number of living bodies is equal to the prescribed number (S124). If the counted number of living bodies is not equal to the prescribed number (NO in S124), the notifier 16 provides notification of a false negative result (S180). For example, in a nursery school, the notifier 16 may notify a nursery teacher of a false negative result via an indicator of a mobile terminal carried by the nursery teacher or an indicator installed in nursery school by using an appropriate feedback, such as sound, vibration, or light. In the measurement situation illustrated in FIG. 4, since the number of living bodies is counted as four while the prescribed number is four, the living body detection device 10 continues to detect a living body without notifying of a false negative.

The operation performed by the living body detection device 10 in a measurement situation different from that illustrated in FIG. 4 is described below.

Figure 8:
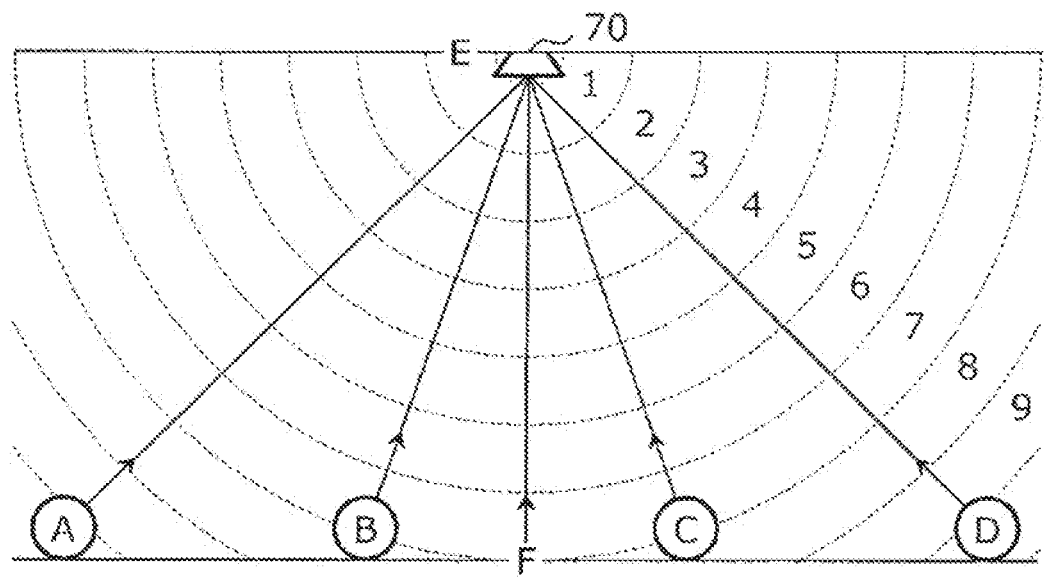
FIG. 8 illustrates another example of the measurement situation according to the first embodiment.

FIG. 8 is a schematic illustration of another example of the measurement situation. The measurement situation illustrated in FIG. 8 differs from the measurement situation illustrated in FIG. 4 in that the positions of the non-contact sensor 70 relative to the target persons A, B, C, and D are changed.

Figure 9:
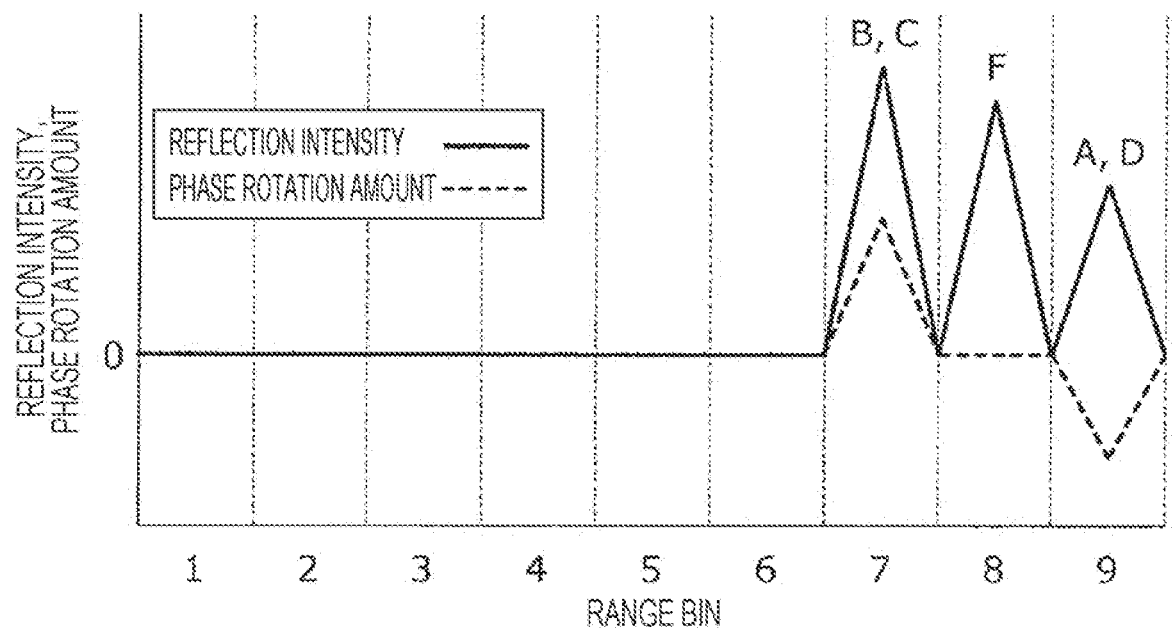
FIG. 9 is a graph illustrating another example of the measurement results according to the first embodiment.

FIG. 9 is a graph illustrating an example of the measurement result corresponding to the measurement situation illustrated in FIG. 8. In the example illustrated in FIG. 9, in the seventh and ninth range bins, the reflection intensities and the phase rotation amounts derived from the target persons B and C and the target persons A and D are detected, respectively. In addition, in the eighth range bin, the reflection intensity derived from the floor F is detected. Since the floor F is stationary, the phase rotation amount derived from the floor F is not detected.

When the non-contact sensor 70 measures a target object in an omnidirectional mode, the reflected waves from the target persons B and C both being present in the seventh range bin mix with each other and, therefore, the target persons B and C cannot be individually detected from the reflection intensity and the phase rotation in the seventh range bin. Similarly, the target persons A and D cannot be individually detected from the reflection intensity and the phase rotation amount in the ninth range bin. That is, the measurement situation illustrated in FIG. 8 is an example of a false negative state in which the non-contact sensor 70 cannot individually detect all the target persons A, B, C, and D.

Figure 10:
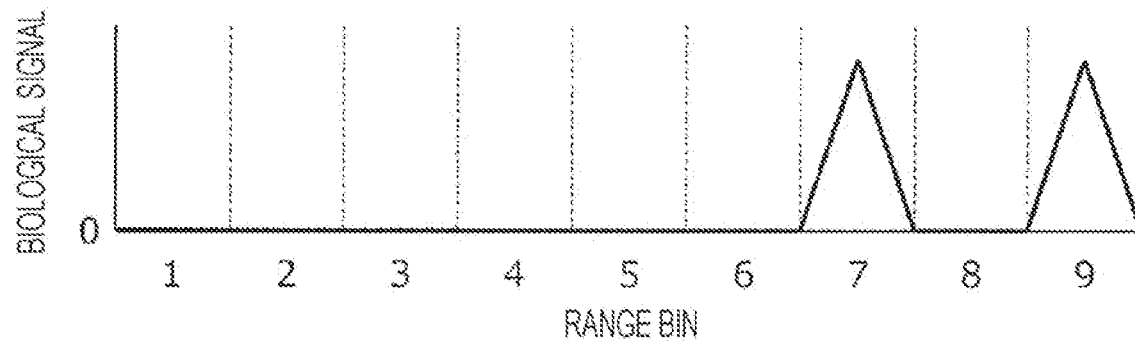
FIG. 10 is a graph illustrating another example of the biological signal according to the first embodiment.

FIG. 10 is a graph illustrating an example of biological signals extracted from the time series of the measurement result illustrated in FIG. 9. In the example illustrated in FIG. 10, the biological signals are extracted in the seventh and ninth range bins. In the eighth range bin, the biological signal is not extracted because the phase rotation amount is not detected. In the example illustrated in FIG. 10, the number of living bodies is counted as two.

In the measurement situation illustrated in FIG. 8, the number of living bodies is counted as two while the prescribed number is four. Therefore, a false negative is found, since the counted number of living bodies is not equal to the prescribed number. The notifier 16 prompts the user to take appropriate measures by notifying the user of a false negative result.

It should be noted that the situation in which the false negative occurs is not limited to the example illustrated in FIG. 8. For example, even in the measurement situation illustrated in FIG. 4, a false negative may occur if a target person moves (e.g., turns over in bed) and, thus, a plurality of target persons enter the same range bin. Even in this case, the notifier 16 can prompt the user to take appropriate measures by notifying the user of a false negative result.

As described above, according to the living body detection device 10, since the measurement result obtained by measuring a target person with the non-contact sensor 70 is used, the target person need not carry any equipment. In addition, since the living body detection device 10 verifies whether the number of living bodies counted from the measurement result of the non-contact sensor 70 is equal to the prescribed number, the living body detection device 10 can find a false negative in the target person detection if the counted number of living bodies is not equal to the prescribed number and perform an appropriate process to take an appropriate measure for the false negative. For example, the living body detection device 10 may notify the user of a false negative result and prompt the user to take an appropriate measure. As a result, a living body detection device capable of reducing the risk of a false negative can be achieved.

Second Embodiment

The processing performed by the living body detection device upon detection of a false negative result is not limited to notification of the false negative result.

According to the second embodiment, a living body detection device including a mover that moves a non-contact sensor is described. If a false negative is detected, the mover moves the non-contact sensor to recover the false negative. Note that the constituent elements and steps similar to those described in the preceding embodiment are identified by the same reference numerals, and a duplicate description is not always provided.

Figure 11:
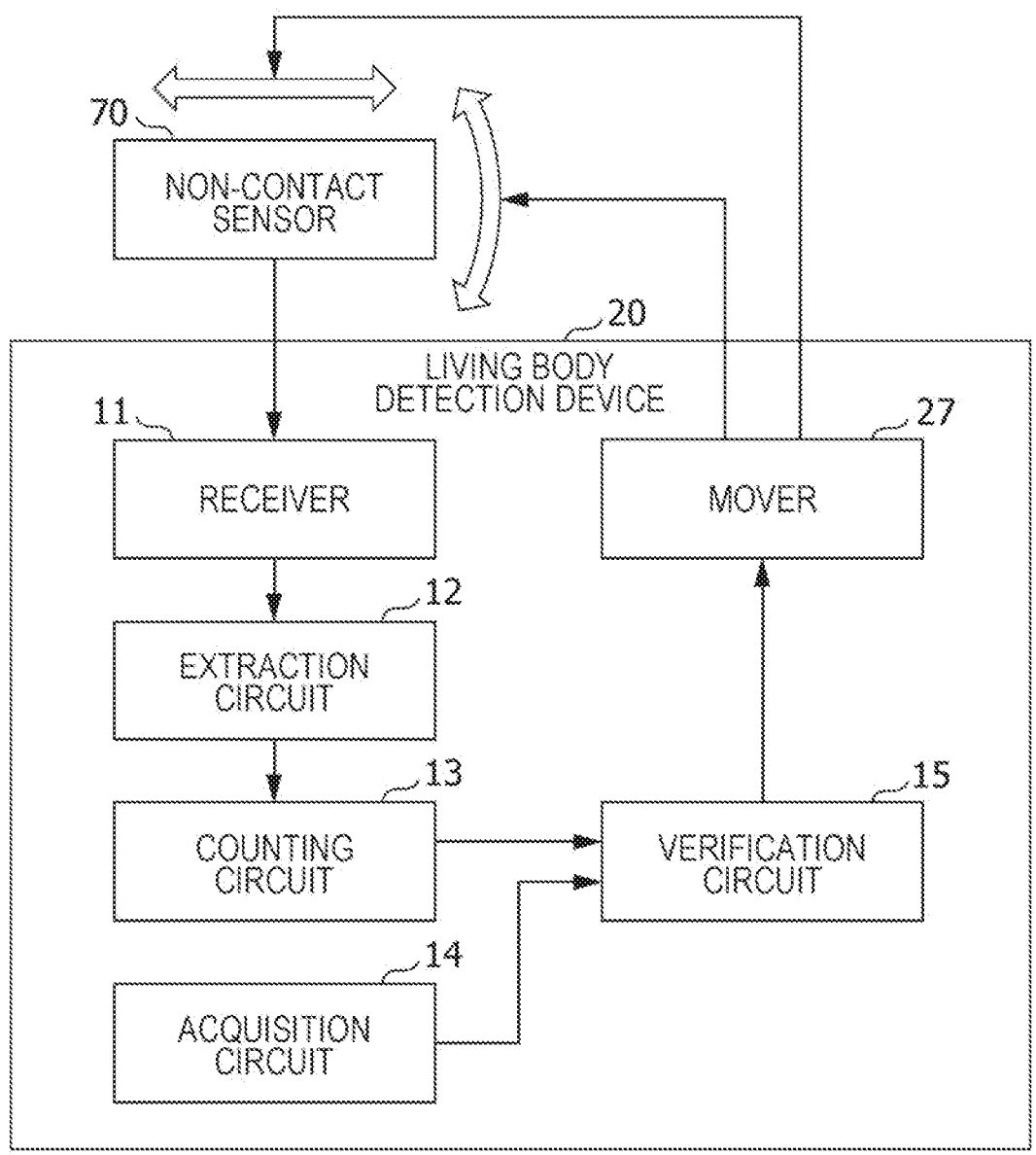
FIG. 11 is a block diagram illustrating an example of the functional configuration of a living body detection device according to the second embodiment.

FIG. 11 is a block diagram illustrating an example of the functional configuration of the living body detection device according to the second embodiment. In a living body detection device 20 illustrated in FIG. 11, a mover 27 is added to and the notifier 16 is removed from the living body detection device 10 illustrated in FIG. 2.

The mover 27 is a moving device that moves the non-contact sensor 70. In FIG. 11, the movement of the non-contact sensor 70 is denoted by white arrows. The mover 27 is not limited to any particular one. The mover 27 may be composed of, for example, a holding unit that holds the non-contact sensor 70 in a movable manner, a power source, and a controller (not illustrated). The holding unit is, for example, a duct rail or a movable stage capable of various movements, such as tilting, rotation, and linear movement. The power source is, for example, an electric motor.

Figure 12:
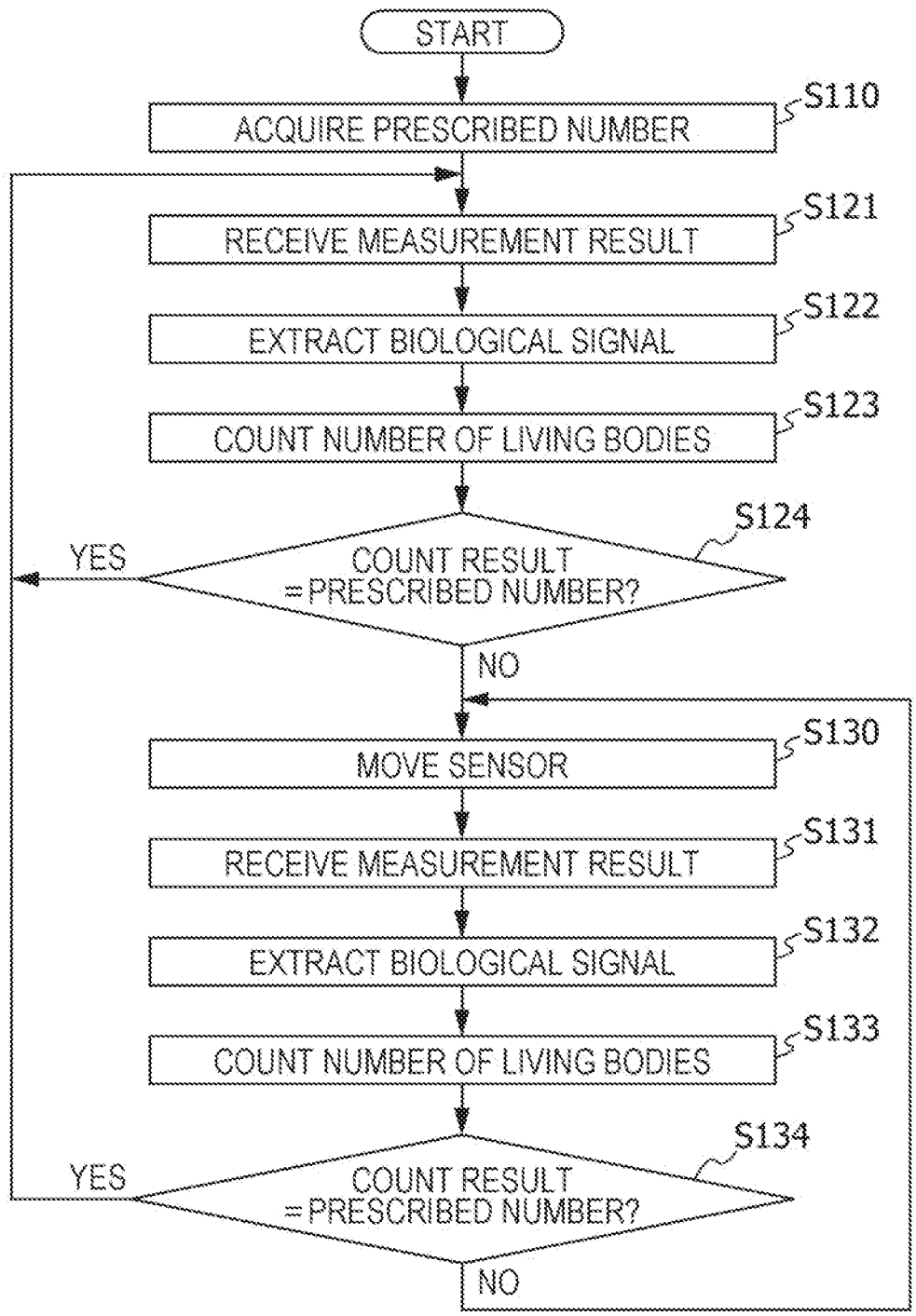
FIG. 12 is a flowchart illustrating an example of the operation performed by the living body detection device according to the second embodiment.

FIG. 12 is a flowchart illustrating an example of the operation performed by the living body detection device 20. In the operation performed by the living body detection device 20 illustrated in FIG. 12, steps S130 to S134 are added to and step S180 is removed from the operation performed by the living body detection device 10 illustrated in FIG. 5.

In the living body detection device 20, like the living body detection device 10, it is determined whether a false negative occurs on the basis of the prescribed number (S110 to S124). The processes in steps S110 to S124 and the measurement situation applied are the same as those described in the first embodiment.

If a false negative is found (NO in S124), the living body detection device 20 instructs the mover 27 to move the non-contact sensor 70 (S130). That is, it can be said that the living body detection device 20 notifies the mover 27 of a false negative result, instead of notifying the user. By moving the non-contact sensor 70, the measurement situation may change and, thus, a false negative may be eliminated.

After moving the non-contact sensor 70, the living body detection device 20 determines again whether a false negative occurs (S131 to S134), and the movement of the sensor and determination of the occurrence of the false negative are repeated until a false negative does not occur (S130 to S134). Although not illustrated, if the false negative cannot be eliminated by moving the non-contact sensor 70 over the entire movable range of the mover 27, the user may be notified of a false negative result.

As described above, if a false negative is detected, the living body detection device 20 can attempt to eliminate a false negative without user intervention by moving the non-contact sensor 70.

Third Embodiment

The processing performed by the living body detection device to eliminate a false negative is not limited to the process to notify the user of a false negative result and the process to move the non-contact sensor.

According to the third embodiment, a living body detection device including a non-contact sensor having both an omnidirectional mode and a directional mode is described. If a false negative is found in the omnidirectional mode, the mode is switched to the directional mode to eliminate the false negative. Note that the constituent elements and steps similar to those described in the preceding embodiments are identified by the same reference numerals, and a duplicate description is not always provided.

Figure 13:
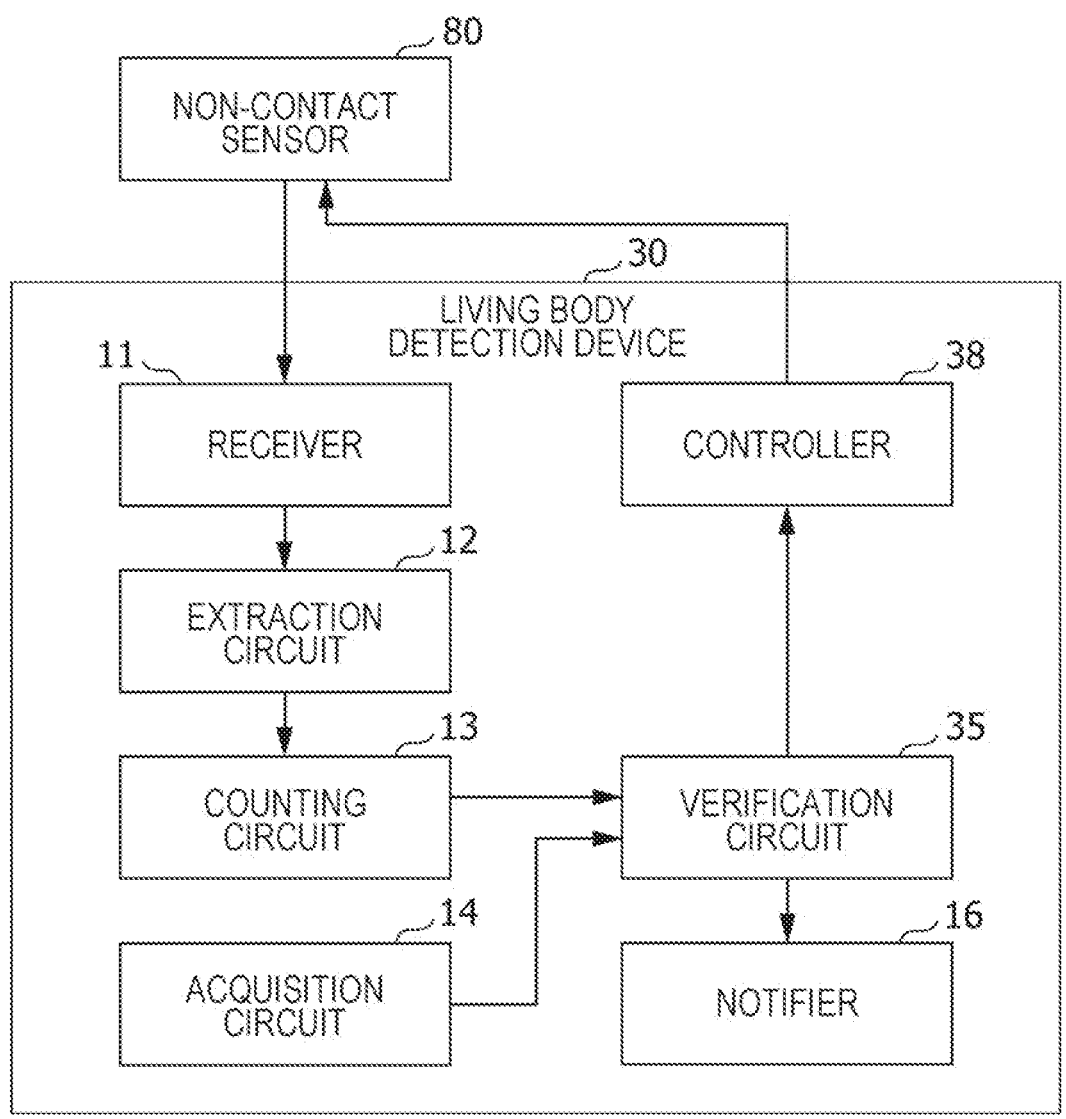
FIG. 13 is a block diagram illustrating an example of the functional configuration of a living body detection device according to a third embodiment.

FIG. 13 is a block diagram illustrating an example of the functional configuration of the living body detection device according to the third embodiment. In a living body detection device 30 illustrated in FIG. 13, as compared with the living body detection device 10 illustrated in FIG. 2, a verification circuit 35 is provided instead of the verification circuit 15, and a controller 38 is added. Furthermore, a non-contact sensor 80 is provided instead of the non-contact sensor 70.

The non-contact sensor 80 has an omnidirectional mode and a directional mode that can be switched under the control of the controller 38.

The omnidirectional mode is a mode in which neither the transmission directivity of the detection wave nor the reception directivity of the reflected wave is controlled. In the omnidirectional mode, the non-contact sensor 80 performs the same operation as the non-contact sensor 70 described above.

The directional mode is a mode for controlling at least one of the transmission directivity of the detection wave and the reception directivity of the reflected wave. In the directional mode, the non-contact sensor 80 can individually detect a plurality of target objects present in the same range bin in different directions by using the directivity.

The directivity is controlled by, for example, a beam forming process using an array antenna. The beam forming process is a process of generating a beam and a null in desired directions by weighting the antenna signal with a complex coefficient for each of antenna elements (that is, by adjusting the amplitude and phase of the antenna signal for each of the antenna element). As used herein, the terms "beam" and "null" directions refer to a direction in which the antenna gain is high and a direction in which the antenna gain is low, respectively.

Figures 14, 15:
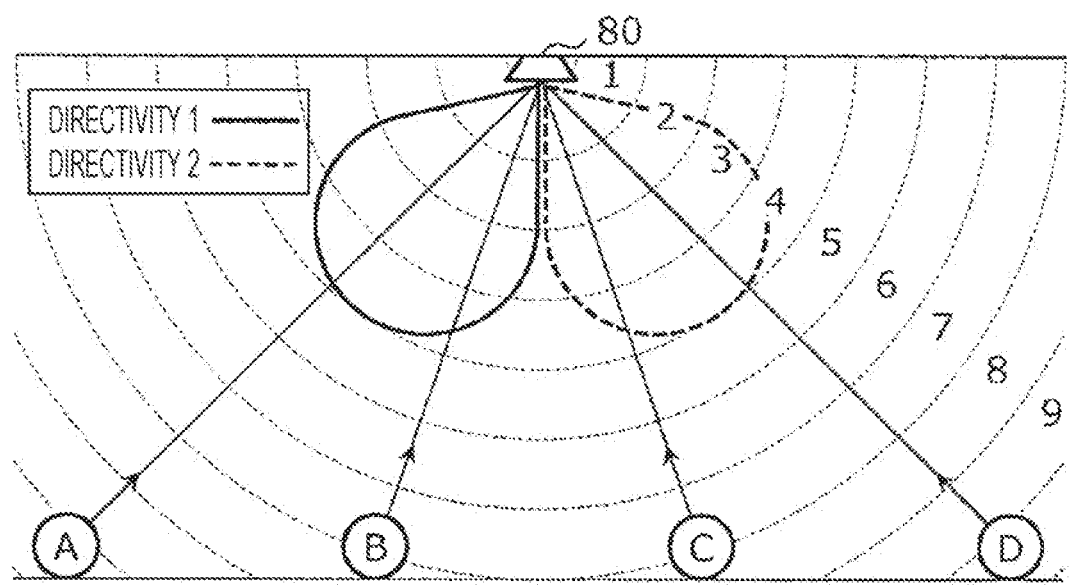
FIG. 14 illustrates an example of a measurement result of a non-contact sensor according to the third embodiment.
FIG. 15 is a schematic illustration of an example of a measurement situation according to the third embodiment.

FIG. 14 is a diagram illustrating an example of a measurement result obtained when the non-contact sensor 80 measures a target object in the directional mode. Note that the measurement result obtained when the non-contact sensor 80 measures a target object in the omnidirectional mode is the same as the measurement result illustrated in FIG. 3. Thus, description of the measurement result is not repeated.

As illustrated in FIG. 14, a measurement result 310 in the directional mode includes a reflection intensity 313 and a phase rotation amount 314 for each of directivities 311 and each of range bins 312. The directivity 311 represents the number used to identify each of different directivities. The range bin 312 represents an index of the distance from the non-contact sensor 80 to the target object. The reflection intensity 313 represents the intensity of the reflected wave from the target object present in the corresponding directional beam direction and also represents the degree of certainty of the target object being present in the corresponding range bin in the corresponding beam direction. The phase rotation amount 314 represents the phase rotation amount between the reflected wave and the detection wave and also represents the relative speed of the target object.

The information portion of the measurement result 310 corresponding to one directivity has the same format as in the measurement result obtained in the omnidirectional mode illustrated in FIG. 3, and the extraction circuit 12 and the counting circuit 13 perform the processing in the same manner as for the measurement result in the omnidirectional mode.

The operation performed by the living body detection device 30 configured as described above is described below with reference to a specific example of the measurement situation.

FIG. 15 is a schematic illustration of an example of the measurement situation. Unlike the measurement situation illustrated in FIG. 8, in the measurement situation illustrated in FIG. 15, the non-contact sensor 80 capable of switching between an omnidirectional mode and a directional mode is used.

FIG. 15 is a schematic illustration of two types of antenna gains representing the directivities used by the non-contact sensor 80 to measure a target object in the directional mode.

In a first directivity (a solid line), a beam is formed in the directions toward the target persons A and B, and a null is formed in the directions toward the target persons C and D. In a second directivity (a dotted line), a beam is formed in the directions toward the target persons C and D, and a null is formed in the directions toward the target persons A and B. Thus, only the target persons A and B are detected in the first directivity, and only the target persons C and D are detected in the second directivity. As described above, according to the directional mode, a plurality of target persons in the same range bin can be individually detected by directivity.

Figure 16:
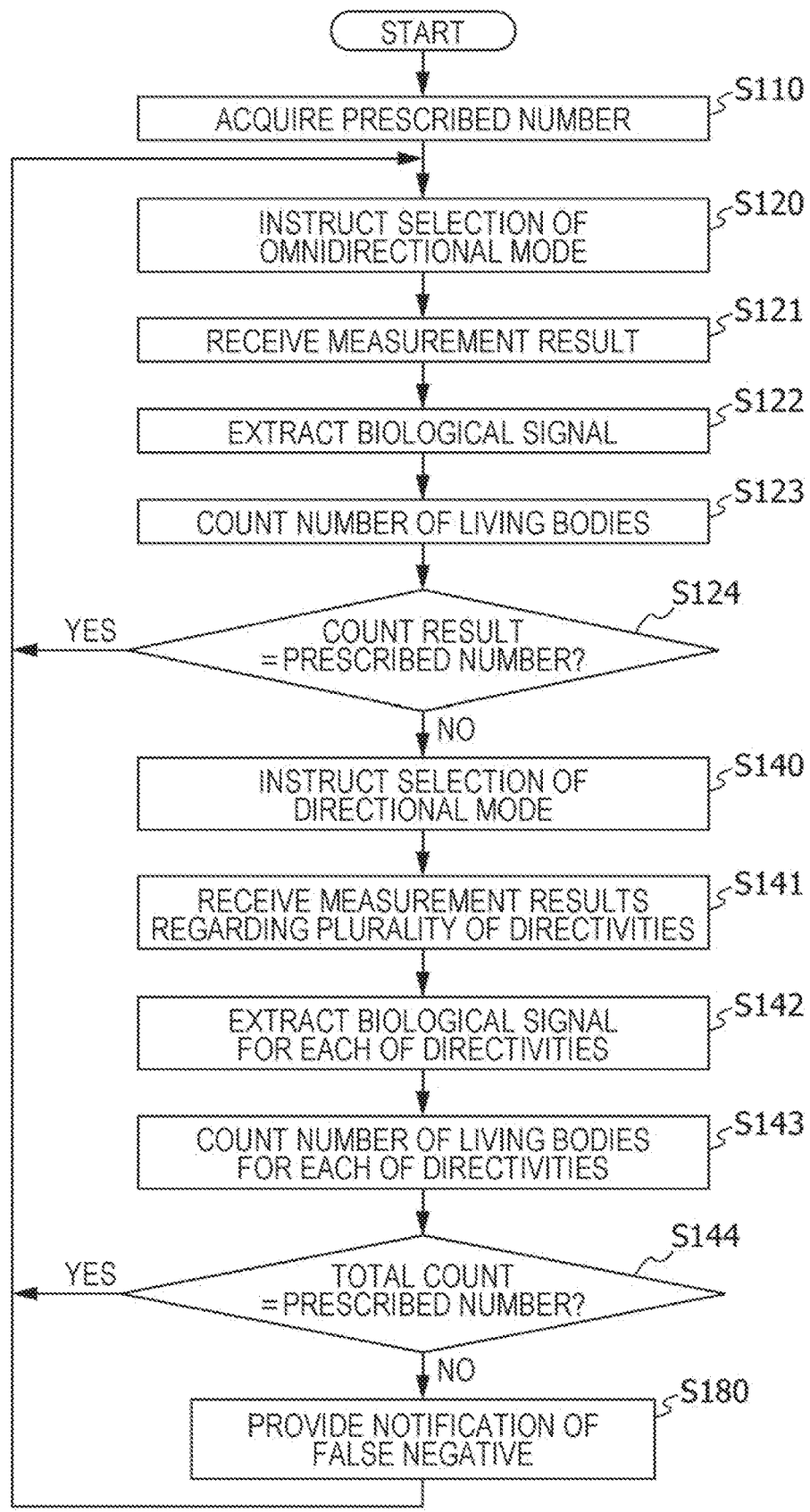
FIG. 16 is a flowchart illustrating an example of the operation performed by the living body detection device according to the third embodiment.

FIG. 16 is a flowchart illustrating an example of the operation performed by the living body detection device 30. In the operation performed by the living body detection device 30 illustrated in FIG. 16, step S120 and steps S140 to S144 are added to the operation performed by the living body detection device 10 illustrated in FIG. 5.

Like the living body detection device 10, the living body detection device 30 determines whether a false negative occurs on the basis of the prescribed number (S110 and S121 to S124). This determination is made on the basis of the measurement result in the omnidirectional mode by the controller 38 that has instructed the non-contact sensor 80 to enter the omnidirectional mode (S120). In the omnidirectional mode, the beam forming process is not performed. This gives the omnidirectional mode an edge over the directional mode in terms of the stability of measurement results, reduction in calculation amount, and reduction in power consumption. For this reason, if it is determined that a false negative does not occur in the omnidirectional mode (YES in S124), the process in the directional mode is not performed.

If a false negative is found in the omnidirectional mode (NO in S124), the controller 38 instructs the non-contact sensor 80 to enter the directional mode (S140). Upon receiving the instruction, the non-contact sensor 80 sequentially forms a plurality of directivities illustrated in FIG. 15, for example. Thereafter, the non-contact sensor 80 measures a target object for each of the formed directivities. The receiver 11 receives, from the non-contact sensor 80, the measurement results regarding the plurality of directivities (S141).

The extraction circuit 12 extracts, from the measurement results, a biological signal for each of the directivities (S142). The counting circuit 13 counts the number of living bodies for each of the directivities from the extracted biological signals (S143).

Figure 17:
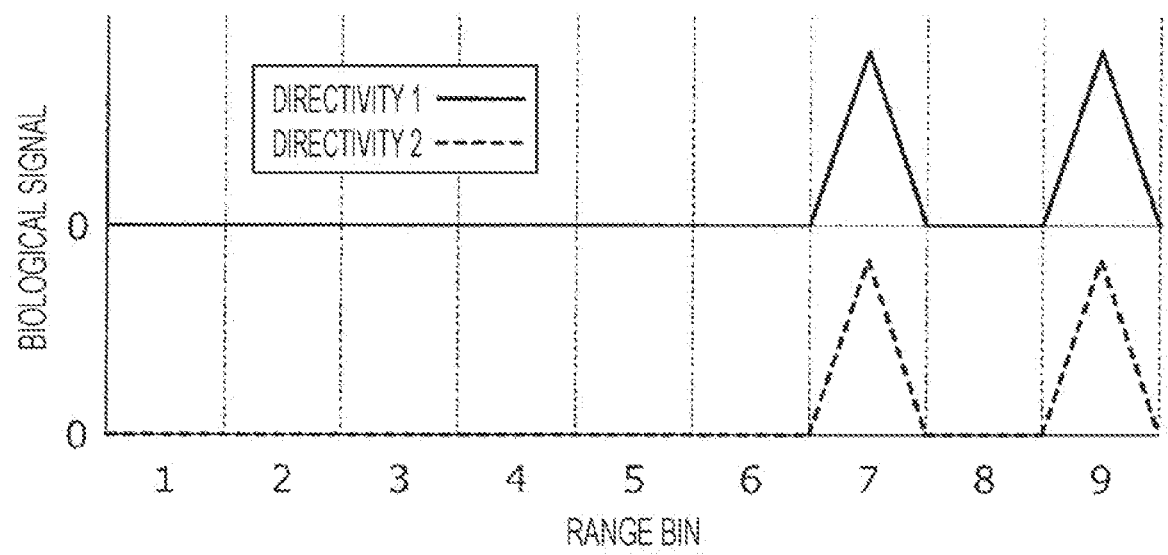
FIG. 17 is a graph illustrating an example of a biological signal according to the third embodiment.

FIG. 17 is a graph illustrating an example of the biological signals extracted for each of the directivities in the measurement situation illustrated in FIG. 15. In the example illustrated in FIG. 17, a biological signal is extracted in each of the seventh and ninth range bins for each of the first directivity (a solid line) and the second directivity (a dotted line). The number of living bodies is counted as two for each of the first directivity and the second directivity.

The verification circuit 35 sums the number of living bodies counted for each of the directivities and verifies whether the total number of living bodies is equal to the prescribed number (S144). If the total number of living bodies is not equal to the prescribed number (NO in S144), the notifier 16 provides notification of the false negative result (S180). In the example of the measurement situation illustrated in FIG. 15, the directional mode is used, and the target persons B and C in the same seventh range bin and the target persons A and D in the same ninth range bin are individually counted by the directivity and are summed up.

As a result, the total count is equal to the prescribed number, and no notification of a false negative result is given.

As described above, according to the living body detection device 30, the non-contact sensor 80 that has found a false negative in the omnidirectional mode is operated in the directional mode, so that the target persons located at the same distance are individually detected by directivity. In this manner, a false negative can be eliminated without user intervention.

Fourth Embodiment

The number of non-contact sensors used to detect a target person is not limited to one. A plurality of non-contact sensors may be used to measure a target person.

According to the fourth embodiment, a living body detection device is described that detects a living body by using a measurement result obtained by measuring a target person with a plurality of non-contact sensors. Note that the constituent elements and steps similar to those described in the preceding embodiments are identified by the same reference numerals, and a duplicate description is not always provided.

Figure 18:
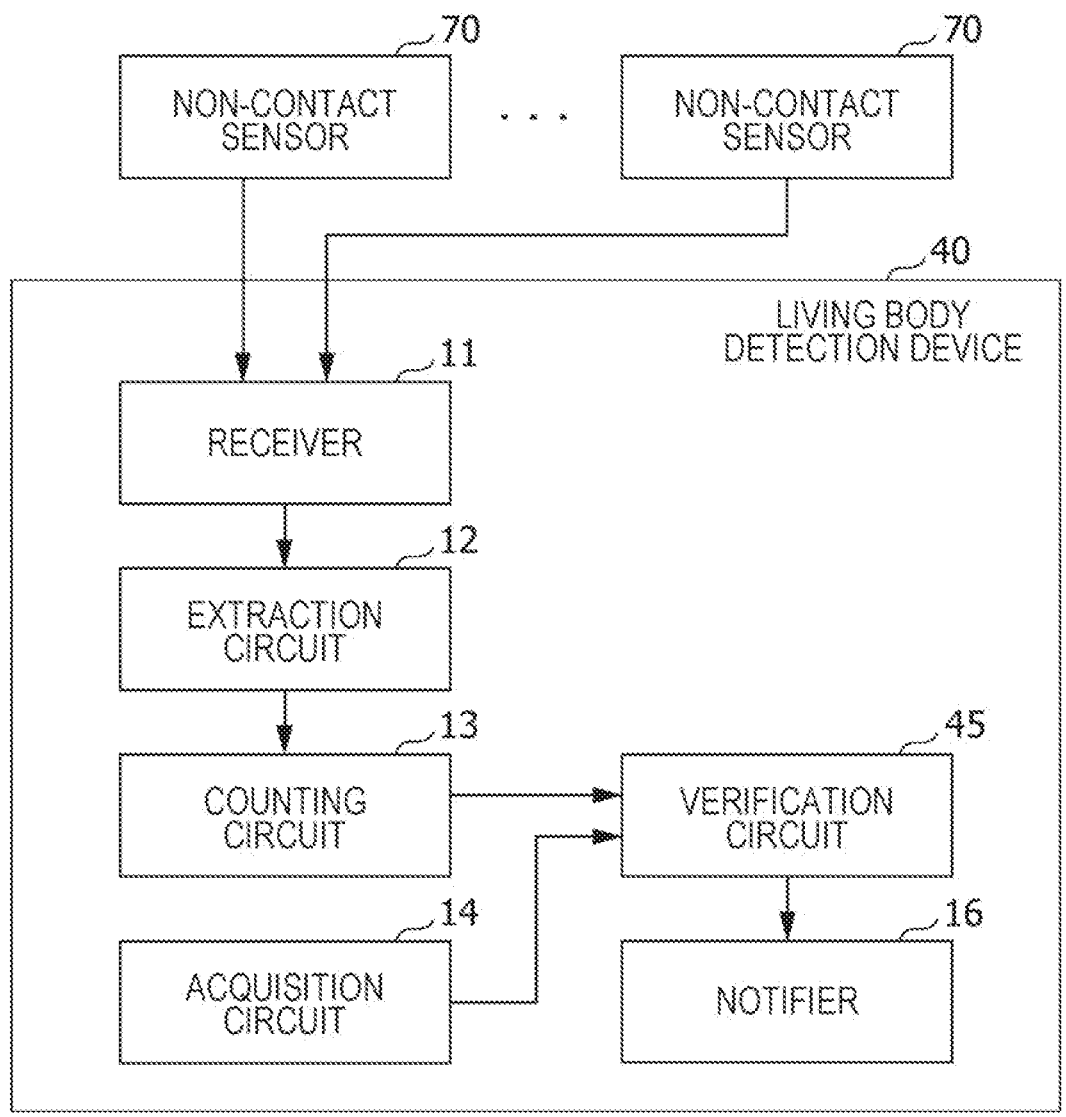
FIG. 18 is a block diagram illustrating an example of the functional configuration of a living body detection device according to the fourth embodiment.

FIG. 18 is a block diagram illustrating an example of the functional configuration of a living body detection device according to the fourth embodiment. Unlike the living body detection device 10 illustrated in FIG. 2, a living body detection device 40 illustrated in FIG. 18 is provided with a verification circuit 45 instead of the verification circuit 15. Furthermore, the living body detection device 40 uses a plurality of non-contact sensors 70. The non-contact sensors 70 may be included in the living body detection device 40.

Figure 19:
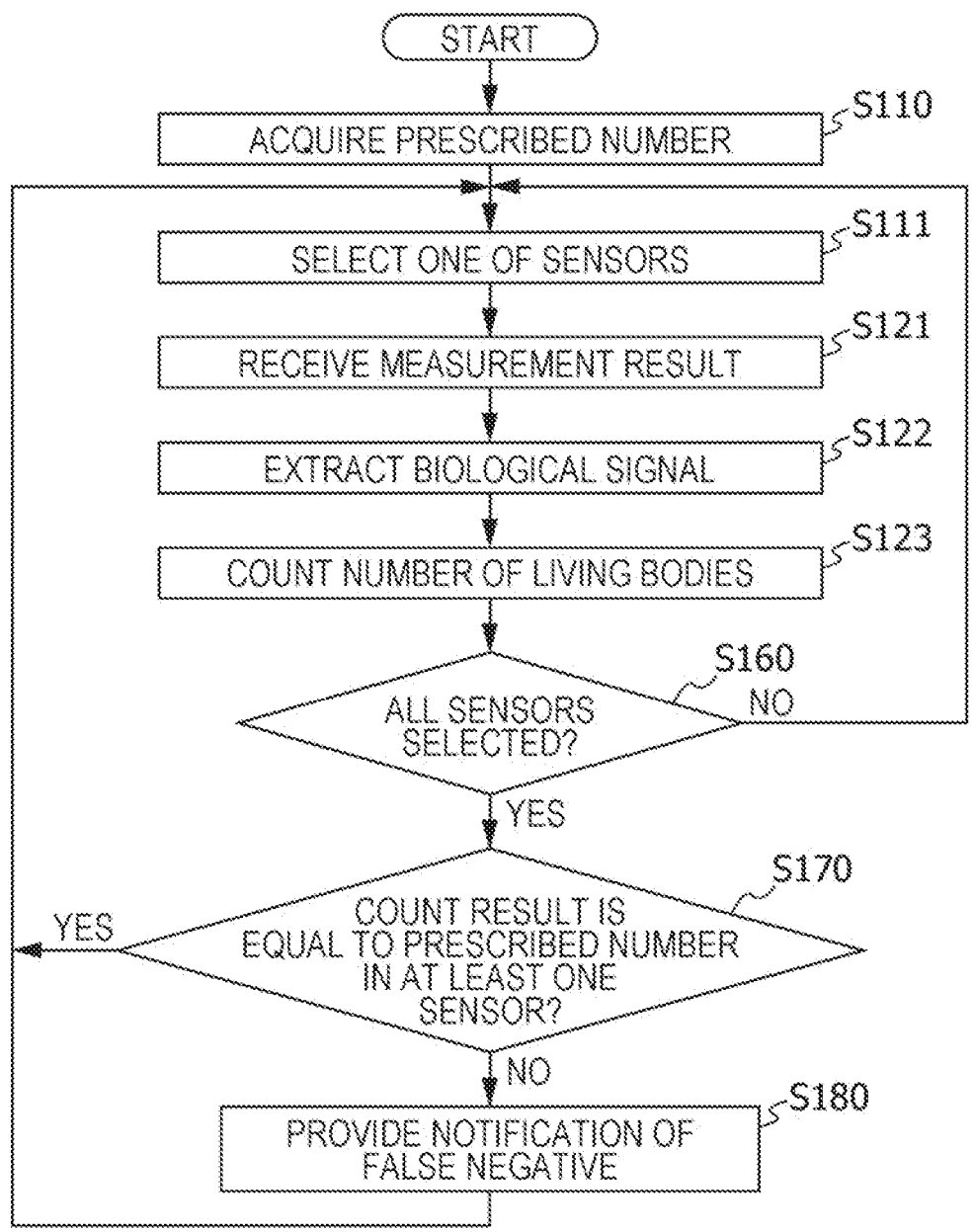
FIG. 19 is a flowchart illustrating an example of the operation performed by the living body detection device according to the fourth embodiment.

FIG. 19 is a flowchart illustrating an example of the operation performed by the living body detection device 40. As compared with the operation performed by the living body detection device 10 illustrated in FIG. 5, in the operation performed by the living body detection device 40 illustrated in FIG. 19, step S124 is removed, and steps S111, S160, and S170 are added.

In the living body detection device 40, a process of selecting one of the non-contact sensors 70 (S111) and a process of counting the number of living bodies in the measurement result output from the selected non-contact sensor 70 (S121 to S123) are repeatedly performed until all the non-contact sensors 70 are selected (S160).

If the number of living bodies is counted for all the non-contact sensors 70 (YES in S160), the verification circuit 45 verifies whether the count result of at least one non-contact sensor 70 is equal to the prescribed number. If at least one non-contact sensor 70 has a count result that is equal to the prescribed number (YES in S170), the living body detection device 40 continues to detect the living body without notifying of a false negative. If the count results of all the non-contact sensors 70 are not equal to the prescribed number (NO in S170), the notifier 16 provides notification of a false negative (S180).

As described above, according to the living body detection device 40, the measurement result obtained by measuring a target person with a plurality of non-contact sensors 70 is used. As a result, a false negative in the target person detection is less likely to occur. In addition, since the living body detection device 40 verifies whether at least one non-contact sensor 70 has a count number of living bodies that is equal to the prescribed number, the living body detection device 40 can find a false negative in the target person detection if the count result is not equal to the prescribed number for all the non-contact sensors 70. As a result, the risk of a false negative in the target person detection can be reduced while avoiding excessive notification of a false negative.

Fifth Embodiment

If the non-contact sensors used to detect the target person have an idle mode, the non-contact sensor that produces a false negative may be run in idle mode.

According to the fifth embodiment, a living body detection device is described in which of the plurality of non-contact sensors, a non-contact sensor having the counted number of living bodies that is not equal to the prescribed number is run in idle mode. Note that the constituent elements and steps similar to those described in the preceding embodiments are identified by the same reference numerals, and a duplicate description is not always provided.

Figure 20:
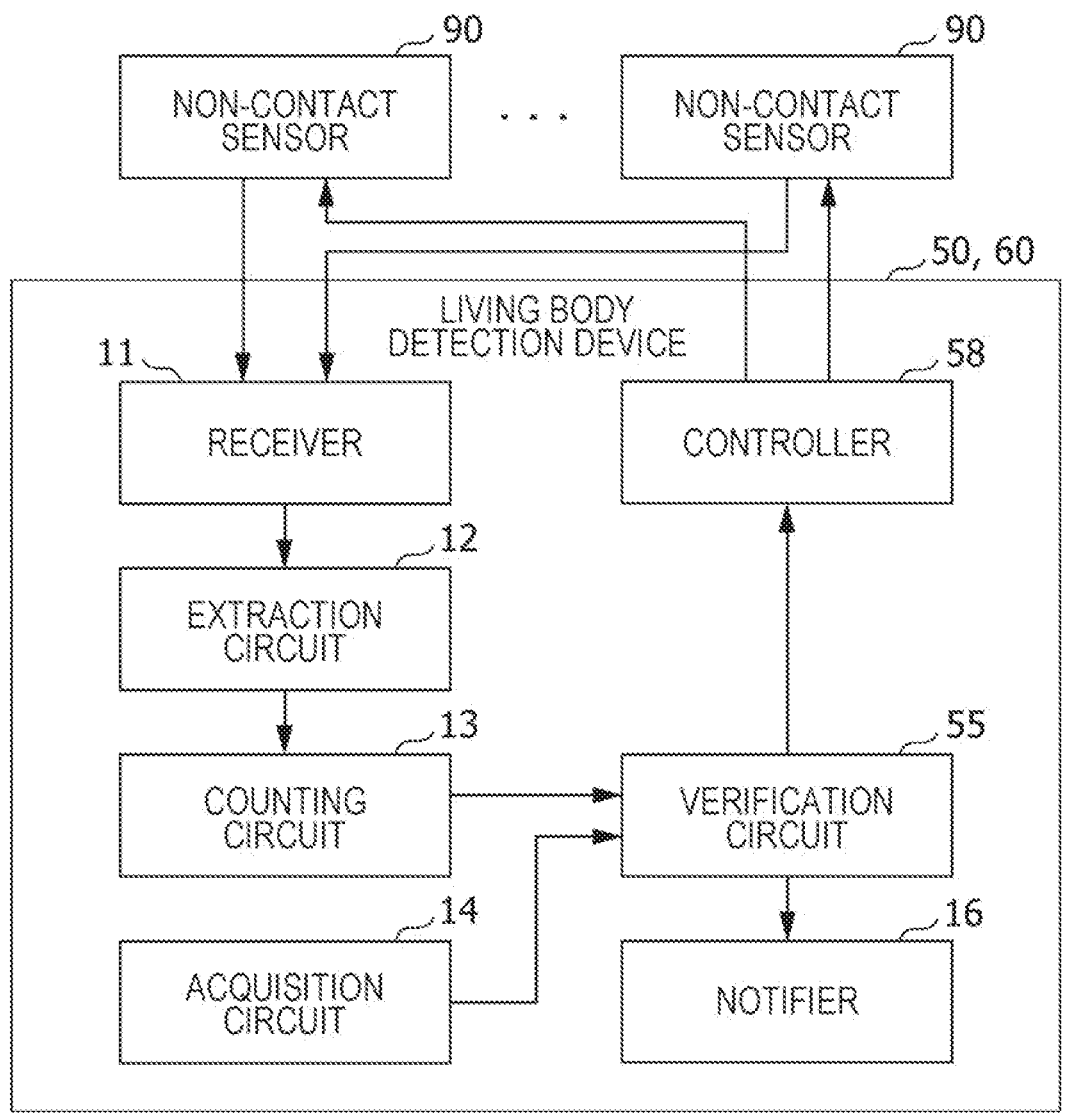
FIG. 20 is a block diagram illustrating an example of the functional configuration of a living body detection device according to the fifth embodiment.

FIG. 20 is a block diagram illustrating an example of the functional configuration of the living body detection device according to the fifth embodiment. Unlike the living body detection device 40 illustrated in FIG. 18, a living body detection device 50 illustrated in FIG. 20 is provided with a verification circuit 55, instead of the verification circuit 45, and an additional controller 58. Furthermore, a plurality of non-contact sensors 90 are provided instead of the plurality of non-contact sensors 70. The plurality of non-contact sensors 90 may be included in the living body detection device 50.

The non-contact sensor 90 has an operation mode and an idle mode that can be switched under the control of the controller 58. The non-contact sensor 90 transmits a detection wave in the operation mode to measure a target object. In addition, the non-contact sensors 90 stops transmission of the detection wave in an idle mode and waits until selection of the operation mode is instructed.

Figure 21:
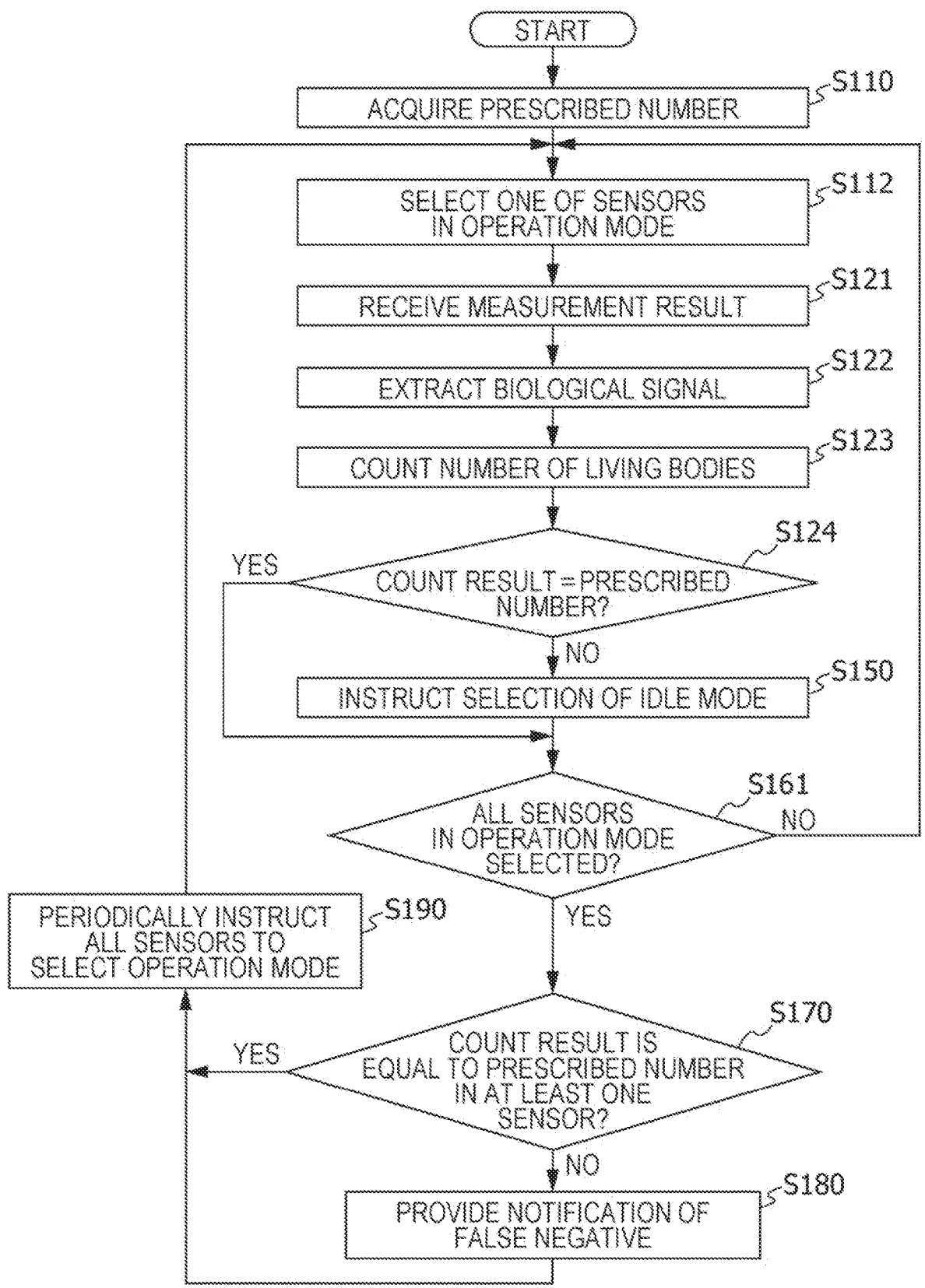
FIG. 21 is a flowchart illustrating an example of the operation performed by the living body detection device according to the fifth embodiment.

FIG. 21 is a flowchart illustrating an example of the operation performed by the living body detection device 50. As compared with the operation performed by the living body detection device 40 illustrated in FIG. 19, in the operation performed by the living body detection device 50 illustrated in FIG. 21, steps S111 and S160 are changed to steps S112 and S161, respectively, and steps S124 and S150 are added.

The living body detection device 50 selects one of the non-contact sensors 90 in the operation mode (S112) and counts the number of living bodies in the measurement result output from the selected non-contact sensor 90 (S121 to S123). If the counted number of living bodies is not equal to a prescribed number (NO in S124), the selected non-contact sensor 90 is instructed to enter the idle mode (S150). This process is repeated until all the non-contact sensors 90 in the operation mode are selected (S161).

If the number of the living bodies is counted for all the non-contact sensors 90 in the operation mode (YES in S161), the verification circuit 55 verifies whether the count result of at least one non-contact sensor 90 is equal to the prescribed number. If at least one non-contact sensor 90 has a count result that is equal to the prescribed number (YES in S170), the living body detection device 50 continues to detect the living body without providing notification of a false negative. However, if the count results of all the non-contact sensors 90 are not equal to the prescribed number (NO in S170), the notifier 16 provides notification of a false negative (S180).

All the non-contact sensors 90 are periodically instructed to enter the operation mode (S190). The instruction to enter the operation mode may be given once for every predetermined number of loop processes by a loop counter or be periodically given by a timer (for example, once every several seconds to several minutes). In this way, the non-contact sensor 90, which can detect all the target persons again due to, for example, the movement of the target person, can enter the operation mode again. As a result, the target persons can be continuously and properly detected.

As described above, according to the living body detection device 50, the target person is detected by the plurality of non-contact sensors 90 and, thus, a false negative in the target person detection is less likely to occur. In addition, since the non-contact sensor 90 that has not detected the prescribed number of target persons is run in idle mode, the power consumption can be reduced, and the amount of electromagnetic radiation absorbed by the target person can be reduced.

Sixth Embodiment

A plurality of non-contact sensors used to detect the target person may have an omnidirectional mode and a directional mode. In this case, the control described in the third embodiment is performed on each of the plurality of non-contact sensors.

According to the sixth embodiment, a living body detection device is described in which of the plurality of non-contact sensors, the non-contact sensor having the number of living bodies counted in the omnidirectional mode that is not equal to the prescribed number is run in directional mode to eliminate a false negative. Note that the constituent elements and steps similar to those described in the preceding embodiments are identified by the same reference numerals, and a duplicate description is not always provided.

The functional configuration of a living body detection device 60 according to the sixth embodiment is substantially the same as the functional configuration of the living body detection device 50 illustrated in FIG. 20. According to the sixth embodiment, it is assumed that each of the plurality of non-contact sensors 90 have both an omnidirectional mode and a directional mode that can be switched under the control of the controller 58. The plurality of non-contact sensors 90 may be included in the living body detection device 60.

Figure 22:
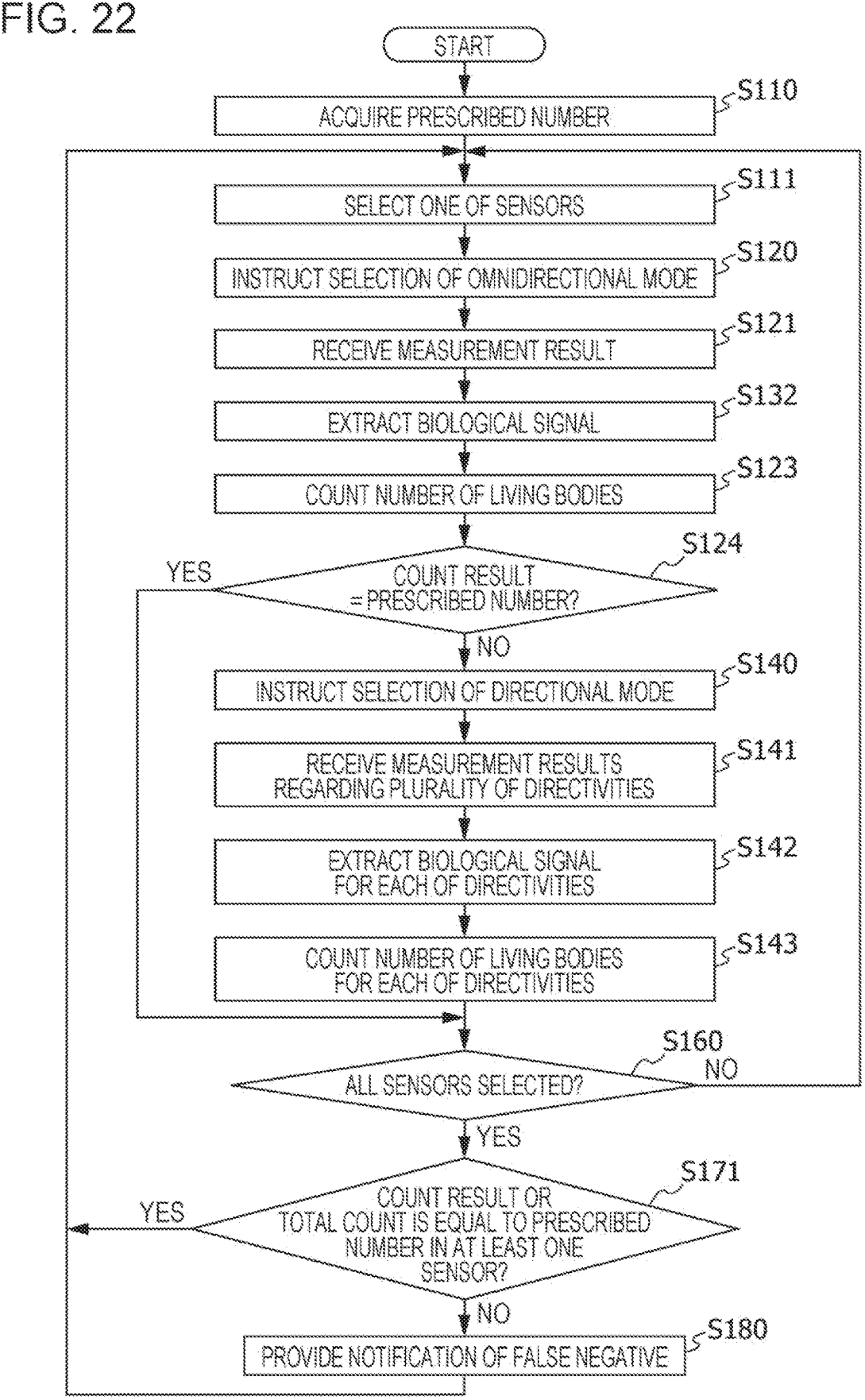
FIG. 22 is a flowchart illustrating an example of the operation performed by a living body detection device according to a sixth embodiment.

FIG. 22 is a flowchart illustrating an example of the operation performed by the living body detection device 60. As compared with the operation performed by the living body detection device 30 illustrated in FIG. 16, in the operation performed by the living body detection device 60 illustrated in FIG. 22, step S144 is removed, and steps S111, S160, and S171 are added.

The living body detection device 60 selects one of the non-contact sensors 90 (S111). Like the living body detection device 30, the number of living bodies is counted in the measurement result output from the selected non-contact sensor 90 in the omnidirectional mode (S120 to S123). If a false negative occurs, the number of living bodies is further counted in the measurement result obtained in the directional mode (S140 to S143). This process is repeated until all the non-contact sensors 90 are selected (S160).

If the number of living bodies is counted for all the non-contact sensors 90 (YES in S160), the verification circuit 55 verifies whether the count result or the total count for at least one non-contact sensor 90 is equal to the prescribed number. If the count result or the total count for at least one non-contact sensor 90 is equal to the prescribed number (YES in S171), the living body detection device 60 continues to detect the living body without notifying of a false negative. However, if neither the count result nor the total count for all the non-contact sensors 90 is equal to the prescribed number (NO in S171), the notifier 16 provides notification of a false negative (S180).

As described above, according to the living body detection device 60, the target person is detected by the plurality of non-contact sensors 90. Consequently, a false negative in the target person detection is less likely to occur. Furthermore, like the living body detection device 30, the non-contact sensor 90 that produces a false negative in the omnidirectional mode is operated in the directional mode. Therefore, by detecting the target persons at the same distance individually by directivity, a false negative can be eliminated without user intervention.

Note that while each of the embodiments of the present disclosure has been described with reference to an example in which the non-contact sensor is disposed on the ceiling is described, the present disclosure is not limited thereto. The non-contact sensor may be installed at a location other than the ceiling by correcting the signal as necessary.

While the living body detection device, the living body detection method, the recording medium, and the program according to the embodiments of the present disclosure have been described above, the present disclosure is not limited to each of the embodiments. A form constructed by making, in the present embodiment, various modifications that a person skilled in the art can conceive and a form constructed by combining the constituent elements in the different embodiments may be encompassed within one or more aspects of the present disclosure.

What is claimed is:

1. A living body detection device, comprising:
   a receiver that receives, from at least one non-contact sensor, a measurement result obtained by measuring a detection area with the at least one non-contact sensor;
   an extraction circuit that extracts a biological signal from the measurement result;
   a counting circuit that counts a number of living bodies present in the detection area based on the biological signal;
   an acquisition circuit that acquires a prescribed number of living bodies to be present in the detection area;
   a verification circuit that verifies whether the number of living bodies counted by the counting circuit is equal to the prescribed number and outputs a result of verification; and
   at least one of a processor or a circuit that moves the at least one non-contact sensor when the number of living bodies counted by the counting circuit is not equal to the prescribed number.

2. The living body detection device according to claim 1, further comprising:
   a notifier that provides notification of a false negative when the number of living bodies counted by the counting circuit is not equal to the prescribed number.

3. The living body detection device according to claim 1, wherein
   the at least one non-contact sensor is capable of switching between a directional mode in which the at least one non-contact sensor has directivity and an omnidirectional mode in which the at least one non-contact sensor does not have directivity, and
   the at least one of the processor or the circuit instructs the at least one non-contact sensor to operate in the directional mode when the number of living bodies counted by the counting circuit is not equal to the prescribed number.

4. The living body detection device according to claim 3, wherein,
   when the at least one non-contact sensor is in the directional mode, the at least one non-contact sensor measures the detection area in a first state having a first directivity and in a second state having a second directivity that is different from the first directivity,
   the receiver receives, from the at least one non-contact sensor, a first measurement result that is obtained in the first state and a second measurement result that is obtained in the second state,
   the extraction circuit extracts a first biological signal from the first measurement result and extracts a second biological signal from the second measurement result,
   the counting circuit counts a first number of living bodies based on the first biological signal and counts a second number of living bodies based on the second biological signal, and
   the verification circuit verifies whether a sum of the first number of living bodies and the second number of living bodies is equal to the prescribed number.

5. The living body detection device according to claim 1, wherein
   the at least one non-contact sensor includes a plurality of non-contact sensors,
   the receiver receives the measurement result from each of the plurality of non-contact sensors,
   the extraction circuit extracts the biological signal from the measurement result output from each of the plurality of non-contact sensors,
   the counting circuit counts the number of living bodies based on the biological signal for each of the plurality of non-contact sensors, and
   the verification circuit further verifies whether at least one of the plurality of non-contact sensors detects the number of living bodies that is equal to the prescribed number.

6. The living body detection device according to claim 5, wherein
   each of the plurality of non-contact sensors is capable of switching between an operation mode in which the living body detection device is capable of measuring the detection area and an idle mode in which the living body detection device does not measure the detection area and is ready for measuring the detection area, and
   the at least one of the processor or the circuit instructs, among the plurality of non-contact sensors, a non-contact sensor that has detected the number of living bodies that is not equal to the prescribed number to enter the idle mode.

7. The living body detection device according to claim 6, wherein the at least one of the processor or the circuit periodically instructs, among the plurality of non-contact sensors, the non-contact sensor in the idle mode to enter the operation mode.

8. The living body detection device according to claim 1, wherein the at least one non-contact sensor is a Doppler radar.

9. A living body detection method, comprising:
   receiving, from at least one non-contact sensor, a measurement result obtained by measuring a detection area with the at least one non-contact sensor;
   extracting a biological signal from the measurement result;

counting a number of living bodies present in the detection area based on the biological signal;

verifying whether the number of living bodies counted in the counting is equal to a prescribed number of living bodies and outputting a result of verification; and causing the at least one non-contact sensor to move when the number of living bodies counted in the counting is not equal to the prescribed number.

10. A non-transitory computer-readable recording medium storing a program, which, when executed by a computer, performs a living body detection method, the living body detection method comprising:

receiving, from at least one non-contact sensor, a measurement result obtained by measuring a detection area with the at least one non-contact sensor;

extracting a biological signal from the measurement result;

counting a number of living bodies present in the detection area based on the biological signal;

verifying whether the number of living bodies counted in the counting is equal to a prescribed number of living bodies and outputting a result of verification; and causing the at least one non-contact sensor to move when the number of living bodies counted in the counting is not equal to the prescribed number.

11. A living body detection device, comprising:

a receiver that receives, from at least one non-contact sensor, a measurement result obtained by measuring a detection area with the at least one non-contact sensor;

an extraction circuit that extracts a biological signal from the measurement result;

a counting circuit that counts a number of living bodies present in the detection area based on the biological signal;

an acquisition circuit that acquires a prescribed number of living bodies to be present in the detection area; and a verification circuit that verifies whether the number of living bodies counted by the counting circuit is equal to the prescribed number and outputs a result of verification, wherein the at least one non-contact sensor is capable of switching between a directional mode in which the at least one non-contact sensor has directivity and an omnidirectional mode in which the at least one non-contact sensor does not have directivity, and the living body detection device further comprises a controller that instructs the at least one non-contact sensor to operate in the directional mode when the number of living bodies counted by the counting circuit is not equal to the prescribed number.

12. The living body detection device according to claim 11, wherein, when the at least one non-contact sensor is in the directional mode, the at least one non-contact sensor measures the detection area in a first state having a first directivity and in a second state having a second directivity that is different from the first directivity, the receiver receives, from the at least one non-contact sensor, a first measurement result that is obtained in the first state and a second measurement result that is obtained in the second state, the extraction circuit extracts a first biological signal from the first measurement result and extracts a second biological signal from the second measurement result, the counting circuit counts a first number of living bodies based on the first biological signal and counts a second number of living bodies based on the second biological signal, and the verification circuit verifies whether a sum of the first number of living bodies and the second number of living bodies is equal to the prescribed number.

13. A living body detection device, comprising:

a receiver that receives, from at least one non-contact sensor, a measurement result obtained by measuring a detection area with the at least one non-contact sensor;

an extraction circuit that extracts a biological signal from the measurement result;

a counting circuit that counts the number of living bodies present in the detection area based on the biological signal;

an acquisition circuit that acquires a prescribed number of living bodies to be present in the detection area; and a verification circuit that verifies whether the number of living bodies counted by the counting circuit is equal to the prescribed number and outputs a result of verification, wherein the at least one non-contact sensor includes a plurality of non-contact sensors, each of the plurality of non-contact sensors is capable of switching between an operation mode in which the living body detection device is capable of measuring the detection area and an idle mode in which the living body detection device does not measure the detection area and is ready for measuring the detection area, and the living body detection device further comprises a controller that instructs, among the plurality of non-contact sensors, a non-contact sensor that has detected the number of living bodies that is not equal to the prescribed number to enter the idle mode.

14. The living body detection device according to claim 13, wherein the controller periodically instructs, among the plurality of non-contact sensors, the non-contact sensor in the idle mode to enter the operation mode.

* * * * *